US010765759B2

(12) United States Patent
Healy et al.

(10) Patent No.: US 10,765,759 B2
(45) Date of Patent: Sep. 8, 2020

(54) METHODS OF TREATING AN OCULAR DISEASE OR DISORDER

(71) Applicant: THE REGENTS OF THE UNIVERSITY OF CALIFORNIA, Oakland, CA (US)

(72) Inventors: Kevin E. Healy, Moraga, CA (US); Eda Isil Altiok, Berkeley, CA (US); David V. Schaffer, Danville, CA (US); Wesley M. Jackson, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 10 days.

(21) Appl. No.: 15/781,395

(22) PCT Filed: Dec. 8, 2016

(86) PCT No.: PCT/US2016/065653
§ 371 (c)(1),
(2) Date: Jun. 4, 2018

(87) PCT Pub. No.: WO2017/100470
PCT Pub. Date: Jun. 15, 2017

(65) Prior Publication Data
US 2018/0318431 A1 Nov. 8, 2018

Related U.S. Application Data

(60) Provisional application No. 62/265,293, filed on Dec. 9, 2015.

(51) Int. Cl.
A61K 39/395 (2006.01)
A61K 47/50 (2017.01)
C07K 19/00 (2006.01)
C07K 16/22 (2006.01)
A61K 47/61 (2017.01)
A61K 9/00 (2006.01)
A61K 38/16 (2006.01)
A61K 47/32 (2006.01)
A61K 47/36 (2006.01)
A61K 9/06 (2006.01)
A61K 38/17 (2006.01)
A61K 47/69 (2017.01)
A61K 38/43 (2006.01)
A61K 39/00 (2006.01)

(52) U.S. Cl.
CPC ............ *A61K 47/61* (2017.08); *A61K 9/0048* (2013.01); *A61K 9/06* (2013.01); *A61K 38/16* (2013.01); *A61K 38/177* (2013.01); *A61K 38/179* (2013.01); *A61K 38/1774* (2013.01); *A61K 38/43* (2013.01); *A61K 39/3955* (2013.01); *A61K 47/32* (2013.01); *A61K 47/36* (2013.01); *A61K 47/6903* (2017.08); *C07K 16/22* (2013.01); *A61K 2039/505* (2013.01);

*C07K 2317/22* (2013.01); *C07K 2317/35* (2013.01); *C07K 2317/622* (2013.01)

(58) Field of Classification Search
None
See application file for complete search history.

(56) References Cited

U.S. PATENT DOCUMENTS

| 9,428,561 B2 | 8/2016 | Healy et al. |
| 9,925,237 B2 | 3/2018 | Healy et al. |
| 2003/0003048 A1 | 1/2003 | Li et al. |
| 2003/0236214 A1 | 12/2003 | Wolff et al. |
| 2004/0038876 A1 | 2/2004 | Pepinsky et al. |
| 2004/0116348 A1 | 6/2004 | Chau et al. |
| 2005/0025752 A1 | 2/2005 | Kutryk et al. |
| 2005/0260651 A1 | 11/2005 | Calias et al. |
| 2006/0094643 A1 | 5/2006 | Svirkin et al. |
| 2006/0171920 A1 | 8/2006 | Shechter et al. |
| 2007/0026518 A1 | 2/2007 | Healy et al. |
| 2008/0113935 A1 | 5/2008 | Yedgar et al. |
| 2010/0104585 A1 | 4/2010 | Kiessling et al. |
| 2010/0210509 A1 | 8/2010 | Oh et al. |

FOREIGN PATENT DOCUMENTS

| WO | WO 2000/045848 | 8/2000 |
| WO | WO 2003/031581 A2 | 4/2003 |
| WO | WO 2005/054860 | 6/2005 |
| WO | WO 2005/110489 | 11/2005 |
| WO | WO 2009/120893 | 10/2009 |

OTHER PUBLICATIONS

Aoyagi, T., et al., "Peptide Drug Carrier: Studies on Incorporation of Vasopressin into Nano-associates Comprising Poly(ethylene glycol)-poly (L-aspartic acid) Block Copolymer", 1999, Colloids and Surfaces B: Biointerfaces, vol. 16, pp. 237-242.
Arpicco, et al.; "Novel Polyethylene glycol derivatives for preparation of Ribosome-Inactivating Protein Conjugates"; Bioconjugate Chem.; vol. 13, pp. 757-765 (2002).
Cairo, et al. "Control of Multivalent Interactions by Binding Epitope Density", J. Am. Chem. Soc., 2002, vol. 124, No. 8, pp. 1615-1619.
Chen, et al. "Mitogenic Activities of Water-Soluble and -Insoluble Insulin Conjugates", Bioconjugate Chem., 1997, vol. 8, pp. 106-110.
Gestwicki, et al., "Influencing Receptor-Ligand Binding Mechanisms with Multivalent Ligand Architecture", J. Am. Chem. Soc., 2002, vol. 124, No. 50.
Glass et al., "Characterization of a hyaluronic acid-Arg-Gly-Asp peptide cell attachment matrix", Biomaterials, 17(11):1101-1108 (1996).
Itoda et al., "Evaluation of the Molecular Recognition of Peptide-Conjugated Polymer", Analytical Sciences, 9:185-187 (2003).

(Continued)

Primary Examiner — Christine J Saoud
Assistant Examiner — Jon M Lockard
(74) Attorney, Agent, or Firm — Bozicevic Field & Francis, LLP; Paula A. Borden

(57) ABSTRACT

The present disclosure provides methods of treating an ocular disease or disorder. The methods involve direct administration into the eye of a conjugate comprising a biologically active polypeptide and a biocompatible polymer.

12 Claims, 22 Drawing Sheets
Specification includes a Sequence Listing.

(56) References Cited

OTHER PUBLICATIONS

Line et al., "Targeting Tumor Angiogenesis: Comparison of Peptide and Polymer-Peptide Conjugates", J Nucl Med, 46(9):1552-1560 (2005).

Mammen, et al. "Polyvalent Interactions in Biological Systems: Implications for Design and Use of Multivalent Ligands and Inhibitors", Angew. Chem. Int. Ed., 1998, vol. 37, pp. 2754-2794.

Mitra, et al.; "Polymer-Peptide Conjugates for angiogenesis targeted tumor radiotherapy"; Nuclear Medicine and Biology; vol. 33, pp. 43-52 (2006).

Smith, et al.; "Conjugation of arginine-glycine-aspartic acid peptides to thermoreversible N-isopropylacrylamide polymers"; Journal of Polymer Science; vol. 41, No. 24, pp. 3989-4000 (Dec. 15, 2003).

Altiok, et al.; "Improving Anti-VEGF Drugs in the Vitreous"; UC Berkeley Ph.D. Thesis; 94 pages (Oct. 2015).

Altiok, et al.; "Multivalent hyaluronic acid bioconjugates improve sFlt-1 activity in vitro"; Biomaterials; vol. 93, pp. 95-105 (2016).

Payne, et al.; "Expression of recombinant canine sFlt1 as an experimental anti-angiogenic agent"; The FASEB Journal; vol. 26, No. 1, Abstract only (Jul. 2012).

Shahangian, et al.; "A conformation-based phage-display panning to screen neutralizing anti-VEGF VHHs with VEGFR2 mimicry behavior"; International Journal of Biological Macromolecules; vol. 77, pp. 222-234 (2015).

Wall, et al.; "Multivalency of Sonic Hedgehog Conjugated to Linear Polymer Chains Modulates Protein Potency"; Bioconjugate Chem.; vol. 19, pp. 806-812 (2008).

Yu, et al.; "Injectable Chemically Crosslinked Hydrogel for the Controlled Release of Bevacizumab in Vitreous: A 6-Month In Vivo Study"; TVST; vol. 4, No. 2, 20 pages (2015).

scale bar = 20um       One-way ANOVA = **

P0-P7 — Normoxia vasculature develops in rat pups

P8-P12 — Hyperoxia vessel loss

P13-P17 — Normoxia initiates neovascularization 2µl treatment scale bar = 250 um scale bar = 100 um One-way ANOVA = ***

At time of injection

Drug residence after time, t

Two-way ANOVA = *

FIG. 11A
FIG. 11B
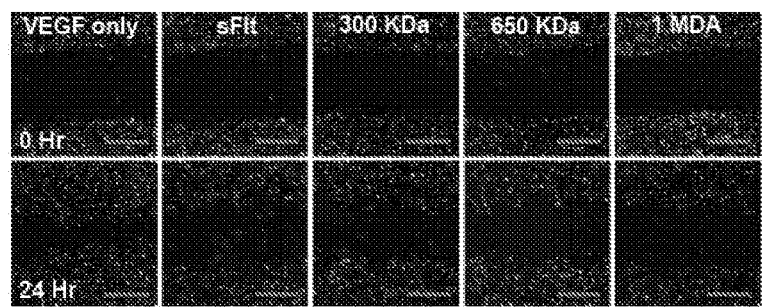
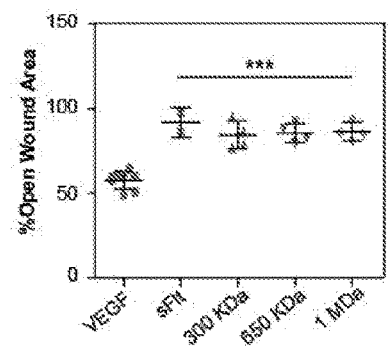

FIG. 12A  FIG. 12B  FIG. 12C
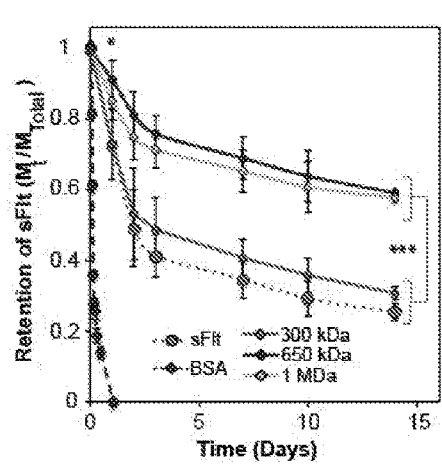
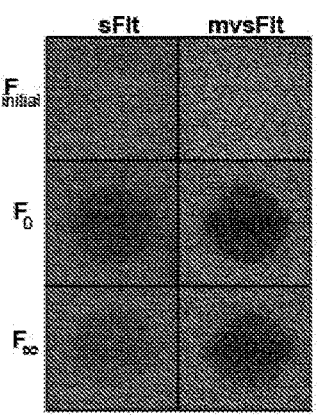
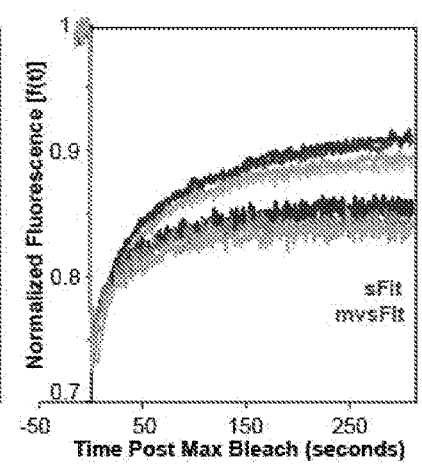

FIG. 16A

```
 26                                              gsklk dpelslkgtq himqagqtlh lqcrgeaahk
 61 wslpemvske serlsitksa cgrngkqfcs tltlntaqan htgfysckyl avptskkket
121 esaiyifisd tgrpfvemys eipeiihmte grelvipcrv tspnitvtlk kfpldtlipd
181 gkriiwdsrk gfiiisnatyk eigiltceat vnghlyktny lthrqtntii dvqistprpv
241 kllrghtlvl nctattplnt rvqmtwsypd eknkrasvrr ridqsnshan ifysvltidk
301 mqnkdkglyt crvrsgpsfk svntsvhiyd kafitvkhrk qqvletvagk rsyrlsmkvk
361 afpspevvwl kdglpateks aryltrgysl iikdvteeda gnytillsik qsnvfknlta
421 tlivnvkpqi yekavssfpd palyplgsrq iltctaygip qptikwfwhp cnhnhsearc
481 dfcsnneesf ildadsnmgn riesitqrma iiegknkmas tlvvadsris giyiciasnk
541 vgtvgrnisf yitdvpngfh vnlekmpteg edklsctvn kflyrdvtwi llrtvnnrtm
601 hysiskqkma itkehsitln ltimnvslqd sgtyacrarn vytgeeilqk keitirdqea
661 pylrnlsdh tvaissttl dchangvpep qitwfknnhk iqqepgiilg pgsstlfier
721 vteedegvyh ckatnqkgsv essayltvqg tsdksnleli tltctcvaat lfwllitlfi
```

(SEQ ID NO:1)

FIG. 16B

```
 26                                              gsklk dpelslkgtq himqagqtlh lqcrgeaahk
 61 wslpemvske serlsitksa cgrngkqfcs tltlntaqan htgfysckyl avptskkket
121 esaiyifisd tgrpfvemys eipeiihmte grelvipcrv tspnitvtlk kfpldtlipd
181 gkriiwdsrk gfiiisnatyk eigiltceat vnghlyktny lthrqtntii dvqistprpv
241 kllrghtlvl nctattplnt rvqmtwsypd eknkrasvrr ridqsnshan ifysvltidk
301 mqnkdkglyt crvrsgpsfk svntsvhi
```

(SEQ ID NO:2)

FIG. 16C

```
142                     ipeiihmte grelvipcrv tspnitvtlk kfpldtlipd
181 gkriiwdsrk gfiiisnatyk eigiltceat vnghlyktny lthrqtntii dvqistprpv
241 kllrghtlvl nctattplnt rvqmtwsypd eknkrasvrr ridqsnshan ifysvltidk
301 mqnkdkglyt crvrsgpsfk svntsvhi
```

(SEQ ID NO:3)

FIG. 17
sFlt amino acid sequence

MVSYWDTGVLLCALLSCLLTGSSGSKLKDPELSLKGTQHIMQAGQTHLQCRGEAAHKWSLPEMV
SKESERLSITKSACGRNGKQFCSTLLNTAQANHIGFYSCKYLAVPTSKKKETESAIYIFISDTGRP
FVEMYSEIPEIHMTEGRELVIPCRVTSPNITVTLKKFPLDTLIPDGKRIIWDSRKGFIISNATYKE
IGLLTCEATVNGHLYKTNYLTHRQTNTIIDVQISTRPVKLLRGHTLVLNCTATTPLNTRVQMTWSY
PDEKNKRASVRRRIDQSNSHANIFYSVLTIDKMQNKDKGLYTCRVRSGPSFKSVNTSVHIYDKAFIT
VKHC<u>DDDDK</u><u>HHHHHH</u>

(SEQ ID NO: 4)

Signal peptide (1-26)
Domain 1 (32-123)
Domain 2 (151-214)
Domain 3 (230-327)
Disulfide bonds: 53-107 ; 158-207 ;
N (100, 164, 196, 251, 323) = glycosylation sites
C = cysteine added (bold and underlined)
DDDDK = glycine linker (double underlined)
HHHHHH = 6His Tag (underlined)

FIG. 18

Anti-VEGF scFv (29.3 kDa):

```
MEIVMTQSPS TLSASVGDRV IITCQASEII HSWLAWYQQK PGKAPKLLIY        50
LASTLASGVP SRFSGSGSGA EFTLTISSLQ PDDFATYYCQ NVYLASTNGA       100
NFGQGTKLTV LGGGGSGGGG GSGGGGSGGG GSEVQLVESG GGLVQPGGSL       150
RLSCTASGFS LTDYYMTWV RQAPGKGLEW VGFIDPDDDP YYATWAKGRF        200
TISRDNSKNT LYLQMNSLRA EDTAVYYCAG GDHNSGWGLD IWGQGTLVTV       250
SSSPSTPPTP SPSTPPGGCD DDKHHHHHH                              280
```

(SEQ ID NO:5)

FIG. 19

Anti-VEGF VHH (16.9 kDa):

```
SNADVQLVES GGGLVQPGGS LRLSCAASGR TFSSYSMGWF RQAPGKEREF        50
VVAISKGGYK YDAVSLEGRF TISRDNAKNT VYLQINSLRP EDTAVYYCAS       100
SRAYGSSRLR LADTYEYWGQ GTLVTVSSSP STPPTPSPST PPGGCDDDDK       150
HHHHHH                                                       156
```

(SEQ ID NO:6)

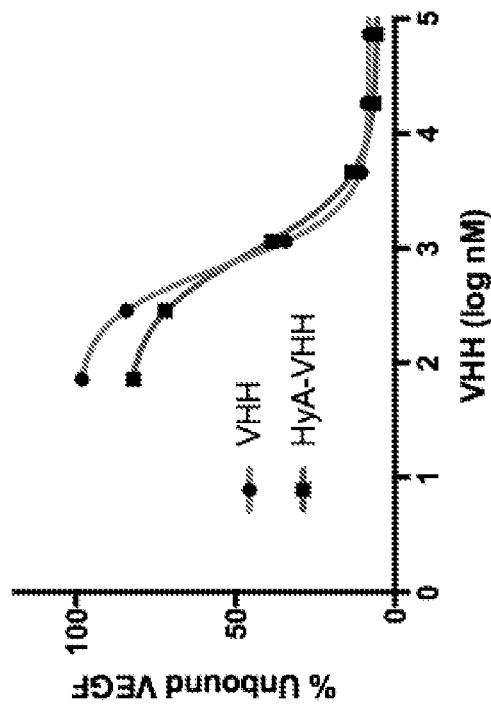
FIG. 20A
FIG. 20B
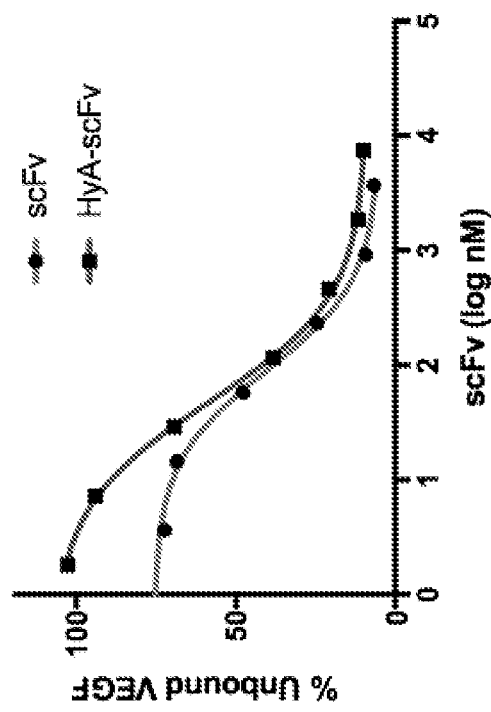
FIG. 20C
|  | Unconjugated | Multivalent Conjugate |
|---|---|---|
| Anti-VEGF scFv | 89.8 nM | 47.7 nM |
| Anti-VEGF VHH | 758.3 nM | 812.0 nM |

METHODS OF TREATING AN OCULAR DISEASE OR DISORDER

CROSS-REFERENCE

This application claims the benefit of U.S. Provisional Patent Application No. 62/265,293, filed Dec. 9, 2015, which application is incorporated herein by reference in its entirety.

INTRODUCTION

Current anti-angiogenic polypeptide drugs for patients with diabetic retinopathy suffer from short residence time in the vitreous of the eye. In order to maintain biologically effective doses of drug for inhibiting retinal neovascularization, patients are required to receive regular monthly injections of drug, which often results in low patient compliance and progression of the disease.

SUMMARY

The present disclosure provides methods of treating an ocular disease or disorder. The methods involve direct administration into the eye of a conjugate comprising a biologically active polypeptide and a biocompatible polymer.

The present disclosure provides a method of treating an ocular disease or disorder in an individual, the method comprising administering to the individual an effective amount of a conjugate comprising: a) a biologically active polypeptide having a molecular weight of from about 5 kDa to about 2000 kDa; and b) a biocompatible polymer having a molecular weight of at least about 50,000 Daltons, wherein the polypeptide is covalently linked to the polymer directly or via a linker, and wherein the molar ratio of the biologically active polypeptide to the polymer is at least about 10:1, wherein said administering is by intravitreal administration. In some cases, the biologically active polypeptide is: i) a receptor; ii) a ligand for a receptor; iii) an antibody; or iv) an enzyme. In some cases, the polymer is a linear polymer comprising multiple subunits selected from hyaluronic acid, acrylic acid, ethylene glycol, methacrylic acid, acrylamide, hydroxyethyl methacrylate, mannitol, maltose, glucose, arabinose, taurine, betaine, modified celluloses, hydroxyethyl cellulose, ethyl cellulose, methyl cellulose, hydroxyethyl methyl cellulose, hydroxypropyl methyl cellulose, carboxymethyl cellulose, modified starches, hydrophobically modified starch, hydroxyethyl starch, hydroxypropyl starch, amylose, amylopectin, oxidized starch, heprosan, heparin, chondroitin, chondroitin sulfate, heparin sulfate, and copolymers thereof. In some cases, the polymer is linear poly(acrylic acid). In some cases, is hyaluronic acid. In some cases, the molar ratio of the biologically active polypeptide to the polymer is from about 10:1 to about 25:1. In some cases, the molar ratio of the biologically active polypeptide to the polymer is from about 25:1 to about 50:1. In some cases, the biologically active polypeptide is an inhibitor of angiogenesis. In some cases, the biologically active polypeptide is a soluble vascular endothelial growth factor (VEGF) receptor, angiostatin, endostatin, vasostatin, or an antibody specific for VEGF. In some cases, the biologically active polypeptide is a soluble vascular endothelial growth factor (VEGF) receptor, and wherein the polymer is hyaluronic acid. In some cases, the hyaluronic acid has a molecular weight of from about 600 kDa to about 700 kDa. In some cases, the molar ratio of the VEGF receptor to the hyaluronic acid is about 20:1. In some cases, the vitreous half-life of the conjugate is at least 7 days. In some cases, the individual is a human. In some cases, the ocular disorder is macular degeneration, choroidal neovascularization, macular edema, retinal neovascularization, proliferative vitreoretinopathy, glaucoma, or ocular inflammation. In some cases, the conjugate is administered once every two months, once every three months, once every 6 months, or once a year. In some cases, the vitreous half-life of the conjugate is at least 5-fold greater than the half-life of the biologically active polypeptide not conjugated to the biocompatible polymer.

BRIEF DESCRIPTION OF THE DRAWINGS

FIG. 11A-11B depict the effect of mvsFlt on $VEGF_{165}$-driven HUVEC migration.

FIG. 12A-12C depict the effect of sFlt conjugation to HyA on mvsFlt mobility and diffusion in HyA gels.

FIG. 16A-16C depict amino acid sequences of biologically active polypeptides.

FIG. 17 depicts the amino acid sequence of an exemplary biologically active polypeptide sFlt.

FIG. 18 depicts the amino acid sequence (SEQ ID NO:5) of an scFv anti-VEGF antibody.

FIG. 19 depicts the amino acid sequence (SEQ ID NO:6) of a VHH anti-VEGF antibody.

FIG. 20A-20C depict binding of unconjugated and conjugated anti-VEGF antibodies to $VEGF\text{-}A_{165}$.

DEFINITIONS

Figure 1:
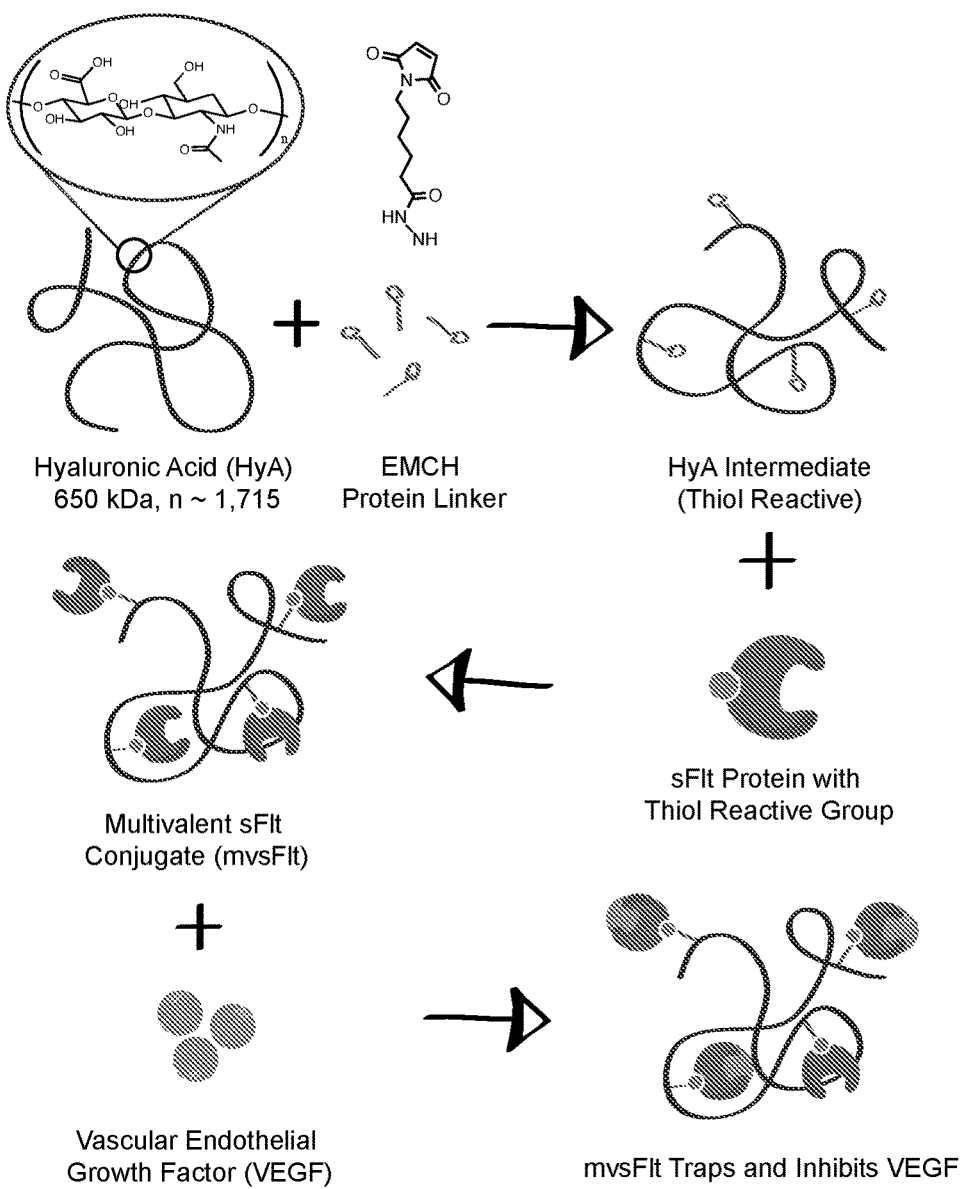
FIG. 1 is a schematic depiction of synthesis of the conjugate mvsFlt.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes polypeptides comprising one or more of a fatty acid moiety, a lipid moiety, a sugar moiety, and a carbohydrate moiety. The term "polypeptides" includes post-translationally modified polypeptides.

The terms "antibodies" and "immunoglobulin" include antibodies or immunoglobulins of any isotype, fragments of antibodies which retain specific binding to antigen, including, but not limited to, Fab, Fv, single chain Fv (scFv), and Fd fragments, chimeric antibodies, humanized antibodies, single-chain antibodies, single domain antibodies (VHH and VANR), and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; single domain antibodies (e.g., camelid antibodies or "VHH" fragments (see, e.g., Harmsen and De Haard (2007) *Appl. Microbiol. Biotechnol.* 77:13); VNAR; and nanobodies; see, e.g., Wesolowski et al. (2009) *Med. Microbiol. Immunol.* 198:157); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "copolymer" describes a polymer which contains more than one type of subunit. The term encompasses polymer which include two, three, four, five, or six types of subunits.

The terms "subject," "individual," "host," and "patient" are used interchangeably herein to a member or members of any mammalian or non-mammalian species. Subjects and patients thus include, without limitation, humans, non-human primates, canines, felines, ungulates (e.g., equine, bovine, swine (e.g., pig)), avians, rodents (e.g., rats, mice), and other subjects. Non-human animal models, particularly mammals, e.g. a non-human primate, a murine (e.g., a mouse, a rat), lagomorpha, etc. may be used for experimental investigations.

"Treating" or "treatment" of a condition or disease includes: (1) preventing at least one symptom of the condition, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a conjugate that, when administered to a mammal or other subject for treating a disease, is sufficient, in combination with another agent, or alone in one or more doses, to effect such treatment for the disease. The "therapeutically effective amount" can vary depending on the conjugate, and depending on one or more other factors, such as the disease and its severity, the age, weight, etc., of the subject to be treated.

The term "unit dosage form," as used herein, refers to physically discrete units suitable as unitary dosages for human and animal subjects, each unit containing a predetermined quantity of a conjugate, calculated in an amount sufficient to produce the desired effect in association with a pharmaceutically acceptable diluent, carrier or vehicle.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a polypeptide-polymer conjugate" includes a plurality of such conjugates and reference to "the ocular disorder" includes reference to one or more ocular disorders and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method of treating an ocular disease or disorder in an individual. The method generally involves administering to an individual in need thereof an effective amount of a conjugate comprising a biologically active polypeptide and a biocompatible polymer, where the administration is directly into the eye, e.g., the administration is intravitreal administration.

The intravitreal injection route is the most efficient method of delivering drug products to structures in the eye that are located in the posterior chamber. Therefore, it is the preferred method of delivering drugs that act on the retina. However, each intravitreal injection carries a risk of causing retinal detachment from as a result of interfering with the integrity of the eye. Adding volume to the posterior chamber causes a rise in intraocular pressure, and there are risk associated with the eye not accommodating to relieve the added pressure. There is also a risk of introducing an infection into the eye. These complications all carry a risk of impaired vision, which must be weighed against the possible benefits of administering a drug using the intravitreal route.

Therefore, there is a strong motivation to improve the residence time of drugs that are designed to be routinely injected into the vitreous via the intravitreal route. Alternatively, it may be practical in some instances to chemically modify and existing drug in order to increase its residence time within the posterior chamber. This strategy has the potential to reduce the frequency of administration of the drug, and as a consequence, to reduce the overall risk of complication due to administering the drug over time. Increasing the duration of bioactivity may also yield enhanced therapeutic outcomes for the drug as well.

A drug that exhibits greater intravitreal residence time may be preferred by the patient as well relative to a drug product that must be administered more frequently for an equivalent therapeutic function. While the intravitreal injection is performed under topical anesthesia and is generally not regarded as painful, it is burdensome for the patient. It must be performed by a clinician, and thus an office visit is required for each administration of the drug. There is typically short-term irritation and blurred vision due to increased tearing. There may also be short tear changes to the appearance of the eye at the vicinity of the injection site. Thus, patients would likely exhibit a preference for an equivalent therapy that would require fewer intravitreal injections.

The need for less frequent injections would also be preferable from the physician's perspective. The intravitreal injections must be performed by an ophthalmologist, and thus this procedure can occupy a substantial portion of their clinic time. The number of patients that are receiving the intravitreal therapy in their practice can be limited by the frequency that each patient must receive the intravitreal injections. Less frequent injection would increase the number patients that are able receive the method of therapy. A longer acting drug would also be preferable to a depot or long-term drug delivery device, as these typically require a longer implantation procedure and access to a procedure room, which may offset the benefits of less frequent administration for the clinician.

A conjugate comprising a biologically active polypeptide and a biocompatible polymer exhibits a half-life in the vitreous that is greater than the half-life in the vitreous of the biologically active polypeptide not conjugated to the biocompatible polymer. The increased half-life of the conjugate in the vitreous confers certain advantages, including, e.g., reduced burden on the patient; reduced number and/or frequency of administrations; increased safety; decreased incidence of infection; increased patient compliance; and increased efficacy. In addition, a conjugate as described herein allows use of polypeptides for treatment of ocular disorders, which polypeptides would not, in unconjugated form, be retained in the eye for a time period suitable for therapy.

In some cases, an effective amount of a conjugate is an amount that is effective to inhibit pathological angiogenesis in the eye of the individual. For example, in some cases, an effective amount of a conjugate is an amount that, when administered in one or more doses, is effective to inhibit pathological angiogenesis in the eye of the individual by at least 10%, at least 15%, at least 20%, at least 25%, at least 30%, at least 40%, at least 50%, at least 60%, at least 70%, or at least 80%, or more than 80%, compared to the degree of pathological angiogenesis in the eye in the absence of treatment with the conjugate, or before treatment with the conjugate.

In some cases, an effective amount of a conjugate is an amount that is effective to reduce intraocular pressure in the eye of the individual. For example, in some cases, an effective amount of a conjugate is an amount that, when administered in one or more doses, is effective to reduce intraocular pressure by at least 10%, at least 15%, at least 20%, at least 25%, at least 30%, at least 40%, at least 50%, at least 60%, at least 70%, or at least 80%, or more than 80%, compared to the intraocular pressure in the eye in the absence of treatment with the conjugate, or before treatment with the conjugate.

In some cases, an effective amount of a conjugate is an amount that is effective to reduce macular edema in the eye of the individual. For example, in some cases, an effective amount of a conjugate is an amount that, when administered in one or more doses, is effective to reduce macular edema by at least 10%, at least 15%, at least 20%, at least 25%, at least 30%, at least 40%, at least 50%, at least 60%, at least 70%, or at least 80%, or more than 80%, compared to the level of macular edema in the eye in the absence of treatment with the conjugate, or before treatment with the conjugate.

In some cases, an effective amount of a conjugate is an amount that is effective to increase visual acuity in an eye of the individual. For example, in some cases, an effective amount of a conjugate is an amount that, when administered in one or more doses, is effective to increase visual acuity in an eye of the individual by at least at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, or at least 10-fold, or more than 10-fold, compared to the visual acuity in the eye in the absence of treatment with the conjugate, or before treatment with the conjugate.

In some cases, an effective amount of a conjugate is an amount that is effective to inhibit progression of an ocular disease in an individual. For example, in some cases, an effective amount of a conjugate is an amount that, when administered in one or more doses, is effective to inhibit progression of an ocular disease in the individual by at least 10%, at least 15%, at least 20%, at least 25%, at least 30%, at least 40%, at least 50%, at least 60%, at least 70%, or more, compared to the progression in the absence of treatment with the conjugate, or before treatment with the conjugate.

For example, is in some cases, an effective amount of a conjugate is an amount that, when administered in one or more doses, is effective to inhibit progression of non-exudative ARMD to exudative ARMD or to inhibit progression of non-exudative ARMD to a more severe form. In some embodiments, an effective amount of a conjugate is an amount that is effective to inhibit progression of early ARMD (AREDS 2) to intermediate ARMD (AREDS 3) or to advanced ARMD (AREDS 4). In some embodiments, an effective amount of a conjugate is an amount that is effective to inhibit progression of intermediate ARMD (AREDS 3) to advanced ARMD (AREDS 4).

In some cases, an effective amount of a conjugate is an amount that is effective to enhance a biological activity of a retinal cell, e.g., where the retinal cell is a photoreceptor, a retinal ganglion cell, a Muller cell, a bipolar cell, an amacrine cell, a horizontal cell, or a retinal pigmented epithelium cell.

Conjugates

In some embodiments, a polypeptide-polymer conjugate (also referred to herein, for simplicity, as a "conjugate") suitable for use in a method of the present disclosure is of the formula:

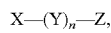

$$X-(Y)_n-Z,$$

where X is a biologically active polypeptide;
Y is an optional linker moiety, such that n is 0 or an integer from 1 to about 10; and
Z is a biocompatible polymer comprising from about 50 subunits to 100,000 subunits, and/or having a molecular weight of from 10 kDa to 500 kDa.

A conjugate comprising a biologically active polypeptide and a biocompatible polymer exhibits a half-life in the vitreous that is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the half-life in the vitreous of the biologically active polypeptide not conjugated to the biocompatible polymer. A conjugate comprising a biologically active polypeptide and a biocompatible polymer exhibits a half-life in the vitreous that is 5-fold to 10-fold greater than the half-life in the vitreous of the biologically active polypeptide not conjugated to the biocompatible polymer.

In some cases, a conjugate comprising a biologically active polypeptide and a biocompatible polymer exhibits a half-life in the vitreous of from about 12 hours to about 24 hours, from about 1 day to about 3 days, from about 3 days to about 7 days, from one week to about 2 weeks, from about 2 weeks to about 4 weeks, or from about 1 month to about 6 months.

In some cases, a conjugate comprising a biologically active polypeptide and a biocompatible polymer exhibits a therapeutically efficacious residence time in the vitreous of from about 12 hours to about 24 hours, from about 1 day to about 3 days, from about 3 days to about 7 days, from one week to about 2 weeks, from about 2 weeks to about 4 weeks, from about 1 month to about 3 months, or from about 3 months to about 6 months.

The biological activity of a polypeptide conjugated to the polymer substrate is enhanced relative to the activity of the polypeptide in soluble form, e.g., compared to the activity of the polypeptide not conjugated to the polymer. In some embodiments, the biological activity of the polypeptide of a polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide in soluble (unconjugated) form.

In some embodiments, the biological activity of the polypeptide of a suitable polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide in when conjugated to the polymer at a 1:1 molar ratio.

In some embodiments, the biological activity of the polypeptide of a suitable polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide when present in admixture with the polymer.

In some cases, the half-maximal effective concentration ($EC_{50}$) of the polypeptide of a subject polypeptide-polymer conjugate is at least about 10%, at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, lower than the $EC_{50}$ of the polypeptide in soluble (unconjugated form).

In some cases, the half-maximal inhibitory concentration ($IC_{50}$) of the polypeptide of a subject polypeptide-polymer conjugate is at least about 10%, at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, lower than the $IC_{50}$ of the polypeptide in soluble (unconjugated form).

Whether the biological activity of the polypeptide of a polypeptide-polymer conjugate is increased relative to the biological activity of the polypeptide in soluble (unconjugated) form is readily determined using an appropriate assay(s) for the biological activity.

The molar ratio of the polypeptide to the polymer can vary from about 5:1 to about 100:1, e.g., from about 5:1 to about 7:1, from about 7:1 to about 10:1, from about 10:1 to about 12:1, from about 12:1 to about 15:1, from about 15:1 to about 20:1, from about 20:1 to about 25:1, from about 25:1 to about 30:1, from about 30:1 to about 35:1, from about 35:1 to about 40:1, from about 40:1 to about 45:1, from about 45:1 to about 50:1, from about 50:1 to about 60:1, from about 60:1 to about 70:1, from about 70:1 to about 80:1, from about 80:1 to about 90:1, or from about 90:1 to about 100:1.

For example, where a polypeptide polymer conjugate comprises a polypeptide that inhibits angiogenesis (e.g., the polypeptide is an anti-angiogenic polypeptide), in some embodiments, the anti-angiogenic polypeptide of a polypeptide-polymer conjugate inhibits angiogenesis by at least about 10%, at least about 15%, at least about 20%, at least about 25%, at least about 30%, at least about 40%, at least about 50%, at least about 60%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, or more, compared to the degree of inhibition of angiogenesis by the anti-angiogenic polypeptide when present in admixture with the polymer, when in soluble (unconjugated) form, or when conjugated to the polymer at a 1:1 molar ratio.

Polymers

Suitable polymers to which a biologically active polypeptide is conjugated include biocompatible polymers comprising from about 50 to about 100,000 subunits, e.g., from about 50 subunits to about 100 subunits, from about 100 subunits to about 500 subunits, from about 500 subunits to about 1,000 subunits, from about 1,000 subunits to about 5,000 subunits, from about 5,000 subunits to about 10,000 subunits, from about 10,000 subunits to about 25,000 subunits, from about 25,000 subunits to about 50,000 subunits, or from about 50,000 subunits to about 100,000 subunits. In some embodiments, the linear polymer comprises more than 100,000 subunits.

Suitable polymers to which a biologically active polypeptide is conjugated include biocompatible polymers having a molecular weight of from 10 kiloDaltons (kDa) kDa to 500 kDa. For example, suitable polymers to which a biologically active polypeptide is conjugated include biocompatible polymers having a molecular weight of from 10 kDa to 15 kDa, from 15 kDa to 20 kDa, from 20 kDa to 25 kDa, from 25 kDa to 50 kDa, from 50 kDa to 75 kDa, from 75 kDa to 100 kDa, from 100 kDa to 125 kDa, from 125 kDa to 150 kDa, from 150 kDa to 200 kDa, from 200 kDa to 250 kDa, from 250 kDa to 300 kDa, from 300 kDa to 350 kDa, from 350 kDa to 400 kDa, from 400 kDa to 450 kDa, or from 450 kDa to 500 kDa. Suitable polymers to which a biologically active polypeptide is conjugated include biocompatible polymers having a molecular weight greater than 500 kDa. Suitable polymers to which a biologically active polypeptide is conjugated include biocompatible polymers having a molecular weight of from 500 kDa to 2 million Daltons (MDa). For example, suitable polymers to which a biologically active polypeptide is conjugated include biocompatible polymers having a molecular weight of from 500 kDa to 750 kDa, from 750 kDa to 1 MDa, from 1 MDa to 1.5 MDa, from 1.5 MDa to 2 MDa, or from 2 MDa to 3 MDa.

In some cases, the subunits are all identical, e.g., the polymer is a homopolymer. In other cases, more than one species of subunit is present, e.g., the polymer is a heteropolymer or copolymer. In some cases, the polymer is a linear polymer. In other cases, the polymer may include one or more branches.

Suitable polymers include natural polymers, semisynthetic polymers, and synthetic polymers.

Suitable natural polymers include hyaluronic acid, collagen, glycosaminoglycans, cellulose, polysaccharides, and the like.

Suitable semisynthetic polymers include, but are not limited to, collagen crosslinked with aldehydes or precursors of the same, dicarboxylic acids or their halogenides, diamines, derivatives of cellulose, hyaluronic acid, chitin, chitosan, gellan gum, xanthan, pectin or pectic acid, polyglycans, polymannan, agar, agarose, natural gums and glycosaminoglycans.

Suitable synthetic polymers include, but are not limited to, polymers or copolymers derived from polydioxane, polyphosphazene, polysulphone resins, poly(acrylic acid), poly(acrylic acid) butyl ester, poly(ethylene glycol), poly(propylene), polyurethane resins, poly(methacrylic acid), poly(methacrylic acid)-methyl ester, poly(methacrylic acid)-n butyl ester, poly(methacrylic acid)-t butyl ester, polytetrafluoroethylene, polyperfluoropropylene, poly N-vinyl carbazole, poly(methyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid) (PGA); poly(D,L-lactic acid) (PLA); copolymers of PGA and PLA; poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

The polymer to which the biologically active polypeptide is conjugated can comprise multiple subunits selected from hyaluronic acid, acrylic acid, ethylene glycol, vinyl, propylene, methyl methacrylate, methacrylic acid, acrylamide, hydroxyethyl methacrylate, tetrafluoroethylene, oxymethylene, a sugar (e.g., glucose, mannitol, maltose, arabinose, etc.), taurine, betaine, modified celluloses, hydroxyethyl cellulose, ethyl cellulose, methyl cellulose, hydroxyethyl methyl cellulose, hydroxypropyl methyl cellulose, carboxymethyl cellulose, modified starches, hydrophobically modified starch, hydroxyethyl starch, hydroxypropyl starch, amylose, amylopectin, oxidized starch, an amino acid, and copolymers of any of the foregoing. In some embodiments, the polymer does not include amino acids. In some cases, the polymer to which the biologically active polypeptide is conjugated comprises heprosan, heparin, chondroitin, chondroitin sulfate, or heparin sulfate.

In some embodiments, the polymer comprises hyaluronic acid or a hyaluronic acid derivative. Hyaluronic acid derivatives include, e.g., a hyaluronic acid ester where part or all of the carboxylic functions are esterified with an alcohol of the aliphatic, aromatic, arylaliphatic, cycloaliphatic or heterocyclic series; a hemiester of succinic acid or a heavy metal salt of the hemiester of succinic acid with hyaluronic acid or with a partial or total ester of hyaluronic acid; sulfated or N-sulfated hyaluronic acid. In some embodiments, the polymer is hyaluronic acid. In some embodiments, the polymer is a hyaluronic acid derivative.

Biologically Active Polypeptides

The size of the polypeptide can range from 2 kDa to about 2000 kDa, e.g., from about 2 kDa to about 5 kDa, from about 5 kDa to about 10 kDa, from about 10 kDa to about 25 kDa, from about 25 kDa to about 50 kDa, from about 50 kDa to about 100 kDa, from about 100 kDa to about 250 kDa, from about 250 kDa to about 500 kDa, from about 500 kDa to about 1000 kDa, from about 1000 kDa to about 2000 kDa.

Biologically active polypeptides that are suitable for inclusion in a conjugate, for use in a method of the present disclosure, include, but are not limited to, a neuroprotective polypeptide, an anti-angiogenic polypeptide, an anti-apoptotic factor, and a polypeptide that enhances function of a retinal cell.

Biologically active polypeptides that are suitable for inclusion in a conjugate, for use in a method of the present disclosure, include, but are not limited to, neuroprotective polypeptides (e.g., GDNF, CNTF, NT4, NGF, and NTN); anti-angiogenic polypeptides (e.g., a soluble vascular endothelial growth factor (VEGF) receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) Mol. Ther. 12:659); an Fc fusion protein comprising a soluble Flt polypeptide (see, e.g., Pechan et al. (2009) Gene Ther. 16:10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-X1); and the like. Suitable polypeptides include, but are not limited to, glial derived neurotrophic factor (GDNF); fibroblast growth factor 2; neurturin (NTN); ciliary neurotrophic factor (CNTF); nerve growth factor (NGF); neurotrophin-4 (NT4); brain derived neurotrophic factor (BDNF); epidermal growth factor; rhodopsin; X-linked inhibitor of apoptosis; and Sonic hedgehog.

Biologically active polypeptides that are suitable for inclusion in a conjugate, for use in a method of the present disclosure, include, but are not limited to, a soluble vascular endothelial growth factor (VEGF) receptor; angiostatin, endostatin; vasostatin; retinal pigment epithelium-specific protein 65 kDa (RPE65); and compstatin. In some cases, the biologically active polypeptide is a soluble fms-like tyrosine kinase-1 (sFlt-1) polypeptide. In some cases, the biologically active polypeptide is a single-domain camelid (VHH) anti-VEGF antibody (VHH anti-VEGF antibody). In some cases, the biologically active polypeptide is a single chain Fv anti-VEGF antibody (scFv anti-VEGF antibody).

Biologically active polypeptides that are suitable for inclusion in a conjugate, for use in a method of the present disclosure, include, but are not limited to, glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, retinoschisin, RPE65, retinitis pigmentosa GTPase-interacting protein-1, peripherin, peripherin-2, a rhodopsin, and Sonic hedgehog.

Suitable polypeptides also include retinoschisin. Suitable polypeptides include, e.g., retinitis pigmentosa GTPase regulator (RGPR)-interacting protein-1 (see, e.g., GenBank Accession Nos. Q96KN7, Q9EPQ2, and Q9GLM3); peripherin-2 (Prph2) (see, e.g., GenBank Accession No. NP_000313; and Travis et al. (1991) Genomics 10:733); peripherin; a retinal pigment epithelium-specific protein (RPE65) (see, e.g., GenBank AAC39660; and Morimura et al. (1998) Proc. Natl. Acad. Sci. USA 95:3088); and the like.

Suitable polypeptides also include: CHM (choroidermia (Rab escort protein 1)), a polypeptide that, when defective or missing, causes choroideremia (see, e.g., Donnelly et al. (1994) Hum. Mol. Genet. 3:1017; and van Bokhoven et al. (1994) Hum. Mol. Genet. 3:1041); and Crumbs homolog 1 (CRB1), a polypeptide that, when defective or missing, causes Leber congenital amaurosis and retinitis pigmentosa (see, e.g., den Hollander et al. (1999) Nat. Genet. 23:217; and GenBank Accession No. CAM23328).

Suitable polypeptides also include polypeptides that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) Ophthalmology 118:160-167); cone photoreceptor cGMP-gated cation channel beta-subunit (CNGB3) (see, e.g., Kohl et al. (2005) Eur J Hum Genet. 13(3):302); guanine nucleotide binding protein (G protein), alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) Nature 461(7265):784-787.

Biologically active polypeptides that are suitable for inclusion in a conjugate, for use in a method of the present disclosure, include an antibody. Suitable antibodies include, e.g., an antibody specific for VEGF; an antibody specific for tumor necrosis factor-alpha (TNF-α); and the like.

Suitable antibodies include, but are not limited to, adalimumab, alemtuzumab, basiliximab, belimumab, bevacizumab, briakinumab, brodalumab, canakinumab, certolizumab, claakizumab, daclizumab, denosumab, efalizumab, epratuzumab, etaracizumab, fezakinumab, figitumumab, fontolizumab, gevokizumab, gotimumab, infliximab, namilumab, namilumab, natalizumab, neutrazumab, nextomab, ocaratuzumab, ofatumumab, olokizumab, pateclizumab, priliximab, ranibizumab, rituximab, secukinumab, sirukumab, sonepcizumab, tabalumab, tocilizumab, toralizumab, ustekinumab, vapaliximab, vedolizumab, veltuzumab, visilizumab, vorsetuzumab, and ziralimumab.

In some cases, the biologically active polypeptide is a soluble fms-like tyrosine kinase-1 (sFlt-1) polypeptide. In some cases, the biologically active polypeptide comprises an amino acid sequence having at least 80%, at least 85%, at least 90%, at least 95%, at least 98%, at least 99%, or 100%, amino acid sequence identity to a contiguous stretch of from 100 amino acids (aa) to 200 aa, from 200 aa to 300 aa, from 300 aa to 400 aa, from 400 aa to 500 aa, from 500 aa to 600 aa, from 600 aa to 700 aa, or from 700 aa to 755 aa, of the amino acid sequence depicted in FIG. 16A. In some cases, the biologically active polypeptide comprises an amino acid sequence having at least 80%, at least 85%, at least 90%, at least 95%, at least 98%, at least 99%, or 100%, amino acid sequence identity to the amino acid sequence depicted in FIG. 16B. In some cases, the biologically active polypeptide comprises an amino acid sequence having at least 80%, at least 85%, at least 90%, at least 95%, at least 98%, at least 99%, or 100%, amino acid sequence identity to the amino acid sequence depicted in FIG. 16C. In some cases, the biologically active polypeptide comprises an amino acid sequence having at least 80%, at least 85%, at least 90%, at least 95%, at least 98%, at least 99%, or 100%, amino acid sequence identity to the amino acid sequence depicted in FIG. 17. In some cases, the biologically active polypeptide comprises the amino acid sequence depicted in FIG. 17. An enterokinase cleavage site (DDDDK; SEQ ID NO:7) and a poly(His) tract (HHHHHH; SEQ ID NO:8) are present at the carboxyl terminus of the amino acid sequence depicted in FIG. 17. In some cases, an sFlt polypeptide does not include an enterokinase cleavage site or a poly(His) tract.

In some cases, the biologically active polypeptide is an sFlt-1 polypeptide having a length of from 150 amino acids to 200 amino acids, from 200 to amino acids to 250 amino acids, from 250 amino acids to 300 amino acids, from 300 amino acids to 350 amino acids, or from 350 amino acids to 400 amino acids.

In some cases, the biologically active polypeptide is a scFv anti-VEGF antibody. Any suitable scFv anti-VEGF antibody can be used. A non-limiting example of an amino acid sequence of a scFv anti-VEGF antibody is provided in FIG. 18. An enterokinase cleavage site (DDDDK; SEQ ID NO:7) and a poly(His) tract (HHHHHH; SEQ ID NO:8) are present at the carboxyl terminus of the scFv anti-VEGF antibody depicted in FIG. 18. In some cases, a scFv anti-VEGF antibody does not include an enterokinase cleavage site or a poly(His) tract.

In some cases, the biologically active polypeptide is a single domain camelid (VHH) anti-VEGF antibody. Any suitable VHH anti-VEGF antibody can be used. A non-limiting example of an amino acid sequence of a VHH anti-VEGF antibody is provided in FIG. 19. An enterokinase cleavage site (DDDDK; SEQ ID NO:7) and a poly(His) tract (HHHHHH; SEQ ID NO:8) are present at the carboxyl terminus of the VHH anti-VEGF antibody depicted in FIG. 19. In some cases, a VHH anti-VEGF antibody does not include an enterokinase cleavage site or a poly(His) tract.

Linkers

As noted above, in some case, a suitable polypeptide-polymer conjugate comprises a linker group that links the polypeptide to the polymer. Suitable linkers include peptide linkers, and non-peptide linkers.

A linker peptide may have any of a variety of amino acid sequences. Exemplary peptide linkers are between about 6 and about 40 amino acids in length, or between about 6 and about 25 amino acids in length. Exemplary linkers include poly(glycine) linkers (e.g., $(Gly)_n$, where n is an integer from 2 to about 10); linkers comprising Gly and Ser; and the like.

Conjugation

A variety of conjugation methods and chemistries can be used to conjugate a polypeptide to a polymer. Various zero-length, homo-bifunctional, and hetero-bifunctional crosslinking reagents can be used. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. Homo- and hetero-bifunctional reagents generally contain two identical or two non-identical sites, respectively, which may be reactive with amino, sulfhydryl, guanidino, indole, or nonspecific groups.

In some embodiments, the polymer comprises an amino-reactive group for reacting with a primary amine group on the polypeptide, or on a linker. Suitable amino-reactive groups include, but are not limited to, N-hydroxysuccinimide (NHS) esters, imidoesters, isocyanates, acylhalides, arylazides, p-nitrophenyl esters, aldehydes, and sulfonyl chlorides.

In some embodiments, the polymer comprises a sulfhydryl-reactive group, e.g., for reacting with a cysteine residue in the polypeptide. Suitable sulfhydryl-reactive groups include, but are not limited to, maleimides, alkyl halides, pyridyl disulfides, and thiophthalimides.

In other embodiments, carbodiimides soluble in both water and organic solvent, are used as carboxyl-reactive reagents. These compounds react with free carboxyl groups forming a pseudourea that can then couple to available amines, yielding an amide linkage.

As noted above, in some embodiments, a polypeptide is conjugated to a polymer using a homobifunctional cross-linker.

In some embodiments, the homobifunctional crosslinker is reactive with primary amines. Homobifunctional crosslinkers that are reactive with primary amines include NHS esters, imidoesters, isothiocyanates, isocyanates, acylhalides, arylazides, p-nitrophenyl esters, aldehydes, and sulfonyl chlorides.

Non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy)ethylsulfone (BSOCOES), bis-2-(sulfosuccinimidooxycarbonyloxy)ethylsulfone (sulfo-BSOCOES), ethylene glycolbis(succinimidylsuccinate) (EGS), ethylene glycolbis(sulfosuccinimidylsuccinate) (sulfo-EGS), dithiobis(succinimidylpropionate (DSP), and dithiobis(sulfosuccinimidylpropionate(sulfo-DSP). Non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)dipropionimidate (DTDP), and dimethyl-3,3'-dithiobispropionimidate (DTBP).

Non-limiting examples of homobifunctional isothiocyanates include: p-phenylenediisothiocyanate (DITC), and 4,4'-diisothiocyano-2,2'-disulfonic acid stilbene (DIDS). Non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate. Non-limiting examples of homobifunctional arylhalides include 1,5-difluoro-2,4-dinitrobenzene (DFDNB), and 4,4'-difluoro-3,3'-dinitrophenyl-sulfone. Non-limiting examples of homobifunctional aliphatic aldehyde reagents include glyoxal, malondialdehyde, and glutaraldehyde. Non-limiting examples of homobifunctional acylating reagents include nitrophenyl esters of dicarboxylic acids. Non-limiting examples of homobifunctional aromatic sulfonyl chlorides include phenol-2,4-disulfonyl chloride, and α-naphthol-2,4-disulfonyl chloride. Non-limiting examples of additional amino-reactive homobifunctional reagents include erythritolbiscarbonate, which reacts with amines to give biscarbamates.

In some embodiments, the homobifunctional crosslinker is reactive with free sulfhydryl groups. Homobifunctional crosslinkers reactive with free sulfhydryl groups include, e.g., maleimides, pyridyl disulfides, and alkyl halides.

Non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl)ether. Non-limiting examples of homobifunctional pyridyl disulfides include 1,4-di-3'-(2'-pyridyldithio)propionamidobutane (DPDPB). Non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylhydrazine, and 1,2-di (bromoacetyl)amino-3-phenylpropane.

As noted above, in some embodiments, a polypeptide is conjugated to a polymer using a heterobifunctional reagent. Suitable heterobifunctional reagents include amino-reactive reagents comprising a pyridyl disulfide moiety; amino-reactive reagents comprising a maleimide moiety; amino-reactive reagents comprising an alkyl halide moiety; and amino-reactive reagents comprising an alkyl dihalide moiety.

Non-limiting examples of hetero-bifunctional reagents with a pyridyl disulfide moiety and an amino-reactive NHS ester include N-succinimidyl-3-(2-pyridyldithio)propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio)toluene (SMPT), divinyl sulfone (DVS), and sulfosuccinimidyl 6-α-methyl-α-(2-pyridyldithio)toluamidohexanoate (sulfo-LC-SMPT).

Non-limiting examples of heterobifunctional reagents comprising a maleimide moiety and an amino-reactive NHS ester include succinimidyl maleimidylacetate (AMAS), succinimidyl 3-maleimidylpropionate (BMPS), N-.gamma.-maleimidobutyryloxysuccinimide ester (GMBS)N-.gamma.-maleimidobutyryloxysulfosuccinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

Non-limiting examples of heterobifunctional reagents comprising an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino) hexanoylamino)hexanoate (SIAXX), succinimidyl-6-(((4-(iodoacetyl)-amino)methyl)-cyclohexane-1-carbonyl) aminohexanoate (SIACX), and succinimidyl-4 ((iodoacetyl)-amino)methylcyclohexane-1-carboxylate (SLAC).

A non-limiting example of a hetero-bifunctional reagent comprising an amino-reactive NHS ester and an alkyl dihalide moiety is N-hydroxysuccinimidyl 2,3-dibromopropionate (SDBP). A non-limiting example of a hetero-bifunctional reagent comprising an alkyl halide moiety and an amino-reactive p-nitrophenyl ester moiety include p-nitrophenyl iodoacetate (NPIA).

Compositions, Formulations, Dosages, and Routes of Administration

In some cases, a method of the present disclosure comprises administering to an individual in need thereof a polypeptide-polymer conjugate, where the polypeptide-polymer conjugate is homogeneous, e.g., all of the polypeptides of the polypeptide-polymer conjugate comprise the same amino acid sequence. For example, in some embodiments, a composition to be administered to an individual comprises a plurality of (e.g., multiple copies of) a polypeptide-polymer conjugate, where each polypeptide-polymer conjugate molecule comprises polypeptides that all have the same amino acid sequence.

In some cases, a method of the present disclosure comprises administering to an individual in need thereof a composition comprising a polypeptide-polymer conjugate, where the composition comprises two or more species of a polypeptide-polymer conjugate, e.g., a composition comprises a first polypeptide-polymer conjugate, where the first polypeptide-polymer conjugate comprises polypeptides of a first amino acid sequence; and at least a second polypeptide-polymer conjugate, wherein the second polypeptide-polymer conjugate comprises polypeptides of a second amino acid sequence that is different from the first amino acid sequence. In some cases, a composition comprises a third or additional polypeptide-polymer conjugates. As one non-limiting example, a first polypeptide-polymer conjugate comprises a first polypeptide that is an anti-angiogenic polypeptide; and a second polypeptide-polymer conjugate that comprises a second polypeptide that inhibits a cell signaling pathway. Various other combinations of first, second, etc., polypeptides can be used. The ratio of the first polypeptide-polymer conjugate to the second polypeptide-polymer conjugate in a composition can be varied, e.g., from about 0:001 to $10^3$ to about $10^3$ to 0.001. Similarly, where a subject composition comprises a first, a second, and a third polypeptide-polymer conjugate, the ratios of the first, second, and third polypeptide-polymer conjugates can be varied.

A composition suitable for use in a method of the present disclosure can comprise, in addition to a polypeptide-polymer conjugate, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

A composition suitable for use in a method of the present disclosure can comprise a polypeptide-polymer conjugate (as described above) and a pharmaceutically acceptable excipient. Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

As used herein, the terms "pharmaceutically acceptable carrier" and "pharmaceutically acceptable excipient" are used interchangeably, and include any material, which when combined with a polypeptide-polymer conjugate does not substantially affect the biological activity of the conjugate, does not induce an immune response in a host, and does not have any substantial adverse physiological effect on the host. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The pharmaceutical compositions may be formulated for a selected manner of administration, including for example, intraocular, e.g., intravitreal administration.

A compositions comprising a conjugate can include an aqueous carrier, e.g., water, buffered water, saline, phosphate-buffered saline, and the like. The compositions may contain pharmaceutically acceptable auxiliary substances as required to approximate physiological conditions, such as pH adjusting and buffering agents, tonicity adjusting agents, wetting agents, detergents and the like.

A composition can be sterilized by conventional sterilization techniques, or may be sterile filtered. The resulting aqueous solutions can be packaged for use as is, or lyophilized, the lyophilized preparation being combined with a sterile aqueous carrier prior to administration. The resulting aqueous solution can be packaged in a glass syringe. The pH of the preparations can range from 3 and 11, e.g., from about pH 5 to about pH 9, or from about pH 7 to about pH 8.

Suitable doses of a conjugate, for use in a method of the present disclosure, include from about 1 µg to about 10 mg, e.g., from about 1 µg to about 5 µg, from about 5 µg to about 10 µg, from about 10 µg to about 20 µg, from about 20 µg to about 25 µg, from about 25 µg to about 50 µg, from about 50 µg to about 100 µg, from about 100 µg to about 150 µg, from about 150 µg to about 250 µg, from about 250 µg to about 500 µg, from about 500 µg to about 750 µg, from about 750 µg to about 1 mg, from about 1 mg to about 5 mg, or from about 5 mg to about 10 mg, per dose. In some cases, suitable doses of a conjugate, for use in a method of the present disclosure, include from 10 mg to 100 mg, e.g., from 10 mg to 20 mg, from 20 mg to 25 mg, from 25 mg to 50 mg, from 50 mg to 75 mg, or from 75 mg to 100 mg, per dose.

In some embodiments, multiple doses of a conjugate are administered. The frequency of administration of a conjugate can vary depending on any of a variety of factors, e.g., severity of the symptoms, etc. For example, in some embodiments, a conjugate is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). In some embodiments, a conjugate is administered once every two months, once every three months, once every 6 months, or once a year.

In some cases, a composition comprising a conjugate is administered by an intravitreal, transcleral, periocular, conjunctival, subtenon, intracameral, subretinal, subconjunctival, retrobulbar, or intracanalicular route of administration. In some cases, a composition comprising a conjugate is administered intravitreally. In some cases, the composition is delivered intravitreally or in close proximity to the posterior segment of the eye. In some cases, the composition is administered intravitreally by injection. In some cases, a composition comprising a conjugate is administered by intraocular injection.

Disorders

Ocular disorders that can be treated using a method of the present disclosure include, but are not limited to, macular degeneration, choroidal neovascularization, macular edema, retinal neovascularization, proliferative vitreoretinopathy, glaucoma, and ocular inflammation.

Ocular diseases that can be treated using a method of the present disclosure include, but are not limited to, acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy and diabetic macular edema), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

In some cases, the ocular disease is glaucoma, retinitis pigmentosa, macular degeneration, retinoschisis, Leber's Congenital Amaurosis, diabetic retinopathy, achromotopsia, or color blindness.

Subjects Suitable for Treatment

Subjects suitable for treatment with a method of the present disclosure include individuals who have been diagnosed as having an ocular disease or disorder, e.g., any of the above-listed ocular diseases or disorders. Subjects suitable for treatment with a method of the present disclosure include individuals who have been treated for an ocular disease or disorder, and who have failed to respond to the treatment.

Individuals suitable for treatment with a method of the present disclosure include individuals with reduced visual acuity due to an ocular disease or disorder. Individuals suitable for treatment with a method of the present disclosure include individuals with abnormally high ocular pressure due to an ocular disease or disorder. Individuals suitable for treatment with a method of the present disclosure include individuals with pathological angiogenesis in an eye due to an ocular disease or disorder.

Visual acuity can be measured using, for example, a Snellen chart, a Bailey-Lovie chart, a decimal progression chart, a Freiburg visual acuity test, a measurement of minimum angle of resolution (MAR) etc. Metamorphopsia (visual distortion) may be measured using an Amsler chart. Contrast sensitivity may be measured using a Pelli-Robson chart. Diagnostic studies include, but are not limited to, standard ophthalmologic examination of the fundus, stereo biomicroscopic examination of the macula, intravenous fundus fluorescein angiography, fundus photography, indocyanine green video-angiography, and optical coherence tomography. A subject displaying an abnormality on one or more of these diagnostic studies (e.g., a subject that falls outside a range that is considered normal for a healthy eye) may be treated in accordance with the present disclosure. For example, subjects may be classified as having early, intermediate, or advanced ARMD in accordance with the classification scheme used in the Age-Related Eye Diseases Study. A subject falling into any of the categories described therein, may be treated in accordance with a method of the present disclosure.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: sFlt Multivalent Conjugates Inhibit Angiogenesis and Improve Half-Life In Vivo To improve the intravitreal residence time of anti-VEGF drugs, multivalent bioconjugates of an anti-VEGF protein were synthesized. The conjugates comprise soluble fms-like tyrosine kinase-1 (sFlt) that is covalently grafted to chains of hyaluronic acid (HyA). The conjugates are termed mvsFlt. Using a mouse corneal angiogenesis assay, it was demonstrated that covalent conjugation to HyA chains does not decrease the bioactivity of sFlt and that mvsFlt is equivalent to sFlt at inhibiting corneal angiogenesis. In a rat vitreous model, it was observed that mvsFlt had significantly increased intravitreal residence time compared to the unconjugated sFlt after 2 days. The calculated intravitreal half-lives for sFlt and mvsFlt were 3.3 and 35 hours, respectively. Furthermore, it was shown that mvsFlt is more effective than the unconjugated form at inhibiting retinal neovascularization in an oxygen-induced retinopathy model, an effect that is most likely due to the longer half-life of mvsFlt in the vitreous. Taken together, the results indicate that conjugation of sFlt to HyA does not affect its affinity for VEGF and this conjugation significantly improves drug half-life. These in vivo results indicate that multivalent conjugation can substantially improve upon drug half-life, and thus the efficacy of currently available drugs that are used in diseases such as diabetic retinopathy, thereby improving patient quality of life.

Materials and Methods

Expression of Soluble Flt-1 Receptor

The sFlt sequence for the first 3 Ig-like extracellular domains of sFlt-1 [13] was cloned into the pFastBac1 plasmid (Life Technologies) and then transformed into DH10Bac E. coli, which were plated on triple antibiotic plates containing kanamycin (50 µg/mL Sigma Aldrich), gentamicin (7 µg/mL, Sigma Aldrich), tetracycline (10 µg/mL, Sigma Aldrich), IPTG (40 µg/mL, Sigma Aldrich) and Bluo-gal (100 µg/mL, Thermo Fisher Scientific). The sFlt gene-containing bacmid was isolated from DH10Bac E. coli (Life Technologies) and transfected into SF9 insect cells for virus production (provided by the Tissue Culture Facility, UC Berkeley). Virus was then used to infect High Five insect cells (provided by the Tissue Culture Facility, UC Berkeley) to induce sFlt protein expression. After 3 days, protein was purified from the supernatant using Ni-NTA agarose beads (Qiagen Laboratories). Recombinant sFlt was eluted from the Ni-NTA beads using an imidazole (Sigma Aldrich) gradient and then concentrated and buffer exchanged with 10% glycerol/PBS using Amicon Ultra-15 mL Centrifugal devices (EMD Millipore). The protein solution was sterile filtered and the concentration was determined by BCA assay (Thermo Fisher Scientific).

mvsFlt Conjugate Synthesis

Conjugation of sFlt to HyA was carried out according to the schematic in FIG. 1, and as described previously ([12, 14-16]. To make thiol-reactive HyA intermediates, 3,3'-N-(ɛ-maleimidocaproic acid) hydrazide (EMCH, Pierce, 1.2 mg/mL), 1-hydroxybenzotriazole hydrate (HOBt, Sigma, 0.3 mg/mL) and 1-ethyl-3-(3-dimethylaminopropyl) carbodiimide hydrochloride (EDC, Pierce, 10 mg/mL) were added to a 3 mg/ml solution of 650 kDa HyA (Lifecore Biotechnology) in 0.1 M 2-(N-morpholino) ethanesulphonic acid (MES) (Sigma) buffer (pH 6.5) and allowed to react at 4° C. for 4 h. The solution was then dialyzed into pH 7.0 phosphate-buffered saline (PBS) containing 10% glycerol. Recombinant sFlt was treated with 2-iminothiolane at 10 molar excess to create thiol groups for conjugation to the maleimide group on EMCH. Activated HyA-EMCH was then added to sFlt at a 1:10 molar ratio (HyA to sFlt) and allowed to react at 4° C. overnight to synthesize the final mvsFlt conjugate. The mvsFlt conjugate was dialyzed with 100 kDa molecular weight cut-off (MWCO) Float-A-Lyzer G2 (Spectrum Labs) in pH 7.0 PBS exhaustively to remove unreacted sFlt. The concentration of mvsFlt was measured using a BCA assay.

FIG. 1: Synthesis of mvsFlt Schematic.

mvsFlt bioconjugates were synthesized using a 3-step reaction in which HyA was reacted with EDC and EMCH to create a thiol reactive HyA-EMCH intermediate. sFlt was then treated with 2-iminothiolane and reacted with the HyA-EMCH intermediate for the synthesis of the final mvsFlt bioconjugate.

Corneal Angiogenesis Assay

All experiments were performed with wild-type 7 to 12-week old male and female littermate FVB/n mice. Mice were maintained under pathogen-free conditions in the UCSF barrier facility and conducted in accordance with procedures approved by the UCSF Institutional Animal Care and Use Committee (IACUC). All experiments were approved by the UCSF IACUC prior to work. Mice were anesthetized by isofluorane inhalation (Abbott Laboratories, Abbott Park, Ill.), 10 mg/kg carprofen (Sigma, St. Louis, Mo.), and by topical application of 0.5% Proparacaine (Bausch & Lomb, Rochester, N.Y.) placed on the cornea. An alkaline burn was created by applying filter paper 2.5 mm in diameter soaked in 0.1N NaOH (Sigma Aldrich) for 30 seconds to the central cornea followed by rinsing with 250 µL of PBS. After the chemical burn treatment, topical 0.5% proparacaine was added to the cornea for anesthesia. Mice were administered 5 µL subconjunctival injections with sFlt (150 µg/ml), mvsFlt (150 µg/ml), or PBS at day 1 and day 3 after burn. Ten days after treatment, eyes were enucleated and the corneas were dissected and fixed in 4% paraformaldehyde overnight at 4° C. Corneas were blocked with 3% BSA and stained with DAPI, rabbit anti-mouse CD31 primary antibody (Santa Cruz Biotechnology) and goat anti-rabbit Alexa Fluor 488 secondary antibody (Life Technologies) for visualization and quantification of blood vessels. Corneas were cut into quadrants and flat-mounted onto glass slides using Fluoromount Mounting Medium (Sigma Aldrich). Imaging was carried out with an automated slide scanner, Zeiss Axioscan Z1 (Zeiss Instruments). Corneal blood vessel coverage was quantified using NIH ImageJ software by comparing the total cornea area to the corneal vascularized area.

Determination of mvsFlt Intravitreal Residence Time

All residence time experiments were performed on 8-week old Brown Norway rats obtained from Charles River Laboratories and treated in accordance with protocols approved by the Institutional Animal Care and Use Committee at UC Berkeley. All experiments were approved by the UC Berkeley IACUC prior to work. Rats were anesthetized using a mixture of ketamine and xylazine (50 mg and 10 mg/kg body weight, respectively) for the surgical procedure. Eyes were injected intravitreally 1 mm behind the limbus with 5 µl of PBS, sFlt or mvsFlt at 1 mg/mL using a 30-gauge Hamilton syringe and monitored daily for signs of inflammation. This concentration was selected to maximize fluorescence in the vitreous and remain in the detection limit of the fluorometer after 48 hours. Rats were sacrificed with $CO_2$ asphyxiation in groups at 0, 4, 12, 24 and 48 hours post injection and eyes were immediately enucleated and placed on dry ice. Frozen vitreous was then extracted from the eye and immersed in 100 µL of RIPA buffer. After shaking on ice for 2 hours, each vitreous sample was homogenized with a Tissue Tearor (Bio Spec Products, Inc.) and the fluorescence measured using a fluorometer (Molecular Devices). Quantification was carried out by normalizing the fluorescence of vitreous samples to the 0 hour vitreous fluorescence readings within their respective group. The half-lives of sFlt and mvsFlt were calculated according to Eq. 1:

$$C_t = C_0 e^{-kt} \quad (1)$$

where is the concentration at time t, $C_0$ is the initial concentration and k is the elimination constant given by Eq. 2:

$$k = \log(2)/t_{1/2} \quad (2)$$

where $t_{1/2}$ is the drug half-life. The values used for calculating $t_{1/2}$ were based on data from the 48-hour time point.

OIR Rat Angiogenesis Model

Pregnant Brown Norway rats were obtained from Charles River Laboratories. All the animal experiments were performed in compliance with the ARVO statement for the Use of Animals in Ophthalmic and Vision Research and approved by the University of Oklahoma Institutional Animal Care and Use Committee. Newborn pups were assigned to PBS, sFlt or mvsFlt treatment groups. Light was cycled on a 12 hour on, 12 hour off schedule and room temperature was maintained at approximately 21 C. Rat pups were exposed to hyperoxia (75% $O_2$) from postnatal day 7 (P7) to P12. The oxygen-treated rats were housed in an incubator connected to an Oxycler Model A4 (Redfield, N.Y.) with oxygen and nitrogen, allowing for adjustment of oxygen concentration to 75%±2%. The rats were placed in the oxygen chamber with enough food and water to sustain them for 5 days. On P12, the animals were returned to room air and administered intravitreal injections with 2 µL per eye of PBS, sFlt or mvsFlt at 150 µg/mL. Rats at P17 were anesthetized and perfused with high-molecular weight FITC-dextran ($2\times10^6$; Sigma-Aldrich, St. Louis Mo.) as described by Smith et al [17]. Retinas were dissected and flat-mounted and the vasculature was imaged using a fluorescence microscope (CKX41; Olympus). Vascular coverage at P17 was quantified using NIH ImageJ by comparing the total retinal area to the area of vascularization.

Statistical Analysis

Values are expressed as means±standard deviations (SD). Statistical analysis was performed with two-tailed t-tests to compare mean values. One-way (with Tukey post-hoc analysis) and two-way ANOVA (with Bonferroni posttest) were also used to compare treatment groups in the quantitative measurements where appropriate (Prism, GraphPad Software). A P-value of less than 0.05 was considered to be statistically significant.

Results sFlt and mvsFlt Equally Inhibit Corneal Angiogenesis

The chemical injury-based corneal angiogenesis model was used to determine whether conjugation of sFlt to HyA reduced the bioactivity of mvsFlt to in comparison to sFlt in vivo. Ten days-post corneal injury, all mice treated with sFlt and mvsFlt displayed similar inhibitory profiles of corneal angiogenesis (FIG. 2). Corneas treated with PBS had 28.8±11.5% blood vessel coverage in contrast to corneas treated with sFlt and mvsFlt, which had 12.8±3.8% and 15.8±7.1% vascular coverage, respectively.

Figure 2A:
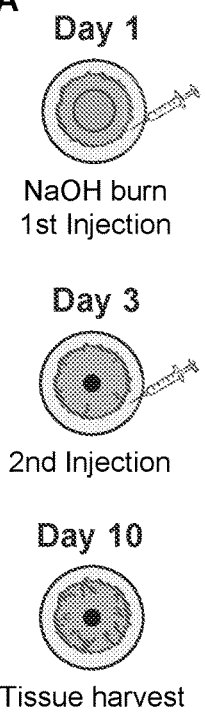
FIG. 2A-2C depict inhibition of corneal angiogenesis by sFlt and mvsFlt.
Figure 2B:
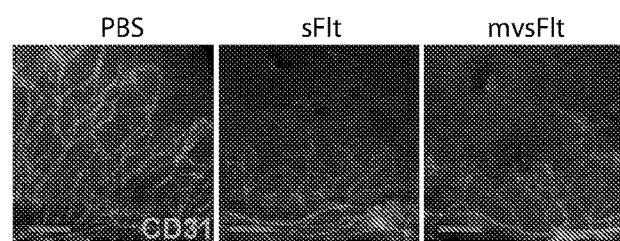
Figure 2C:
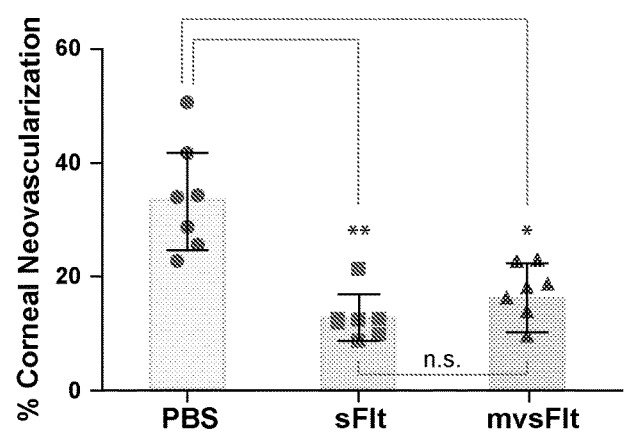

FIG. 2A-2C: sFlt and mvsFlt Equally Inhibit Corneal Angiogenesis.

A) Schematic depicting methods utilized for carrying out corneal burn model. Mice were treated twice with 5 µl of PBS, sFlt or mvsFlt at day 1 and 3 following the chemical burn. B) Representative images of eyes treated with PBS, sFlt and mvsFlt. CD31 positive (green) staining of corneal blood vessels. C) Quantification of corneal angiogenesis at day 10 following treatment. One-way ANOVA gives p value **<0.01 (n.s.—not significant; *p<0.05; **p<0.01). Scale bars correspond to 20 µm.

mvsFlt has Significantly Longer Residence Time In Vitreous

Figure 6:
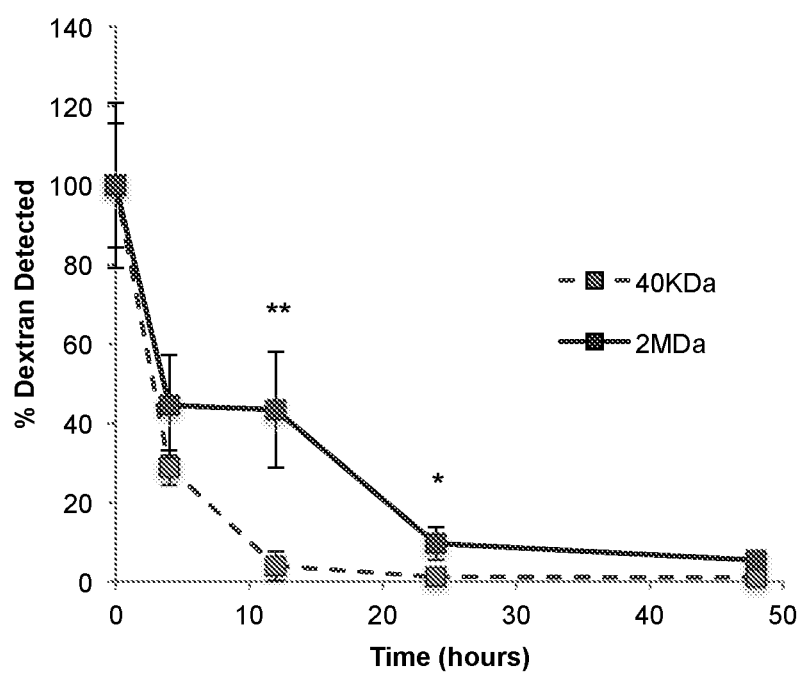
FIG. 6 depicts in vivo residence time of higher molecular weight dextran.
Figure 7A:
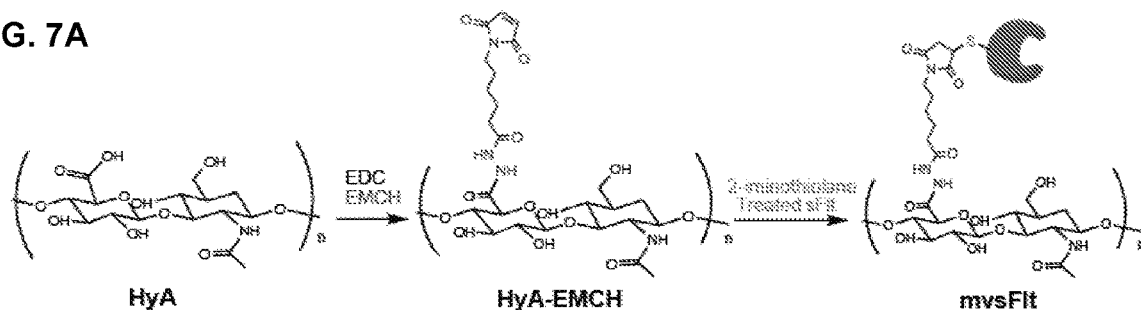
FIG. 7A-7D depict multivalent sFlt synthesis and schematics.
Figure 7B:
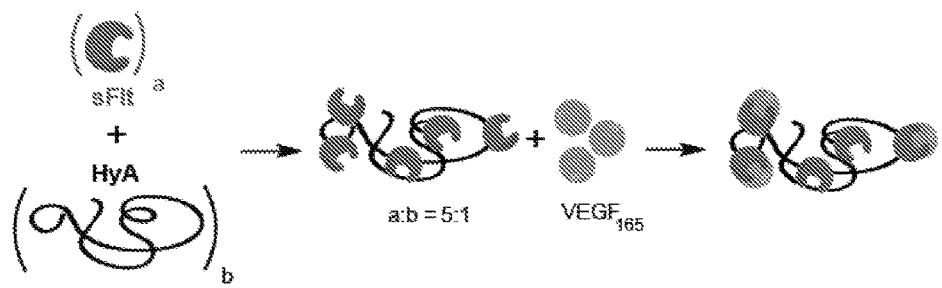
Figure 7C:
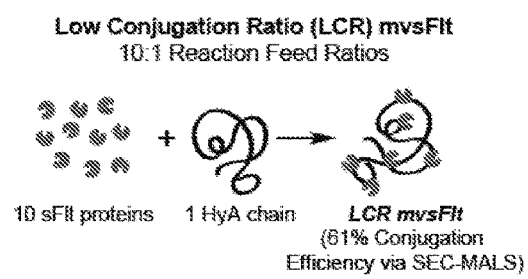
Figure 7D:
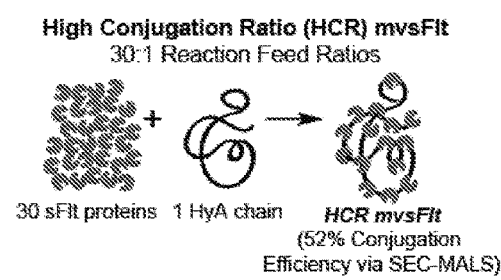

It was confirmed that the vitreous of Brown Norway rats could be used to determine intravitreal residence time of different sized molecules using fluorescently tagged dextrans of varying sizes (FIG. 6). Differences in residence time between sFlt and mvsFlt were immediately apparent beginning at 4 hours where only 18.2±7.3% of sFlt remained compared to 105.8±9.8% of mvsFlt (FIG. 3). By 12 hours, only 2.6±1.9% of sFlt remained detectable compared to 62.9±14.1% of mvsFlt. By 2 days post injection, sFlt was almost undetectable (1.2±0.5%) whereas 66.2±28.6% of mvsFlt remained in the vitreous. The half-life of sFlt in the vitreous was calculated using Eq. 1 and Eq. 2 to be 3.3 hours compared to 35 hours for mvsFlt.

Figure 3A:
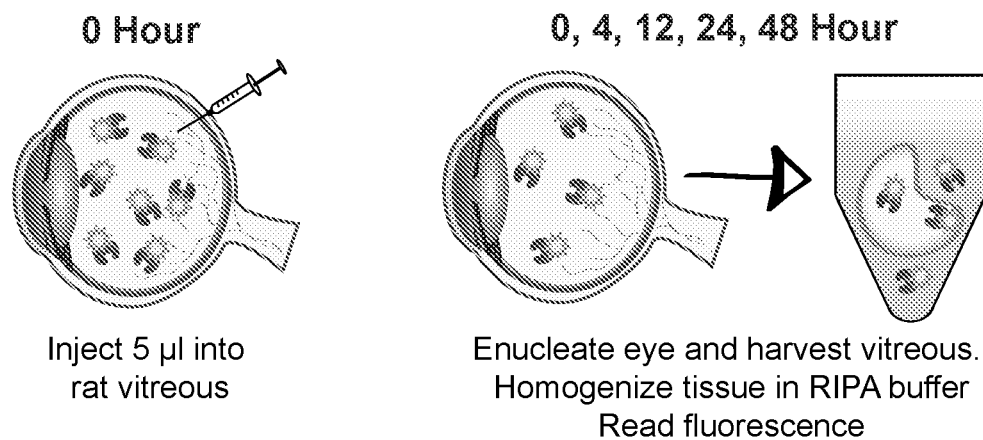
FIG. 3A-3B depict residence time of mvsFlt in the rat vitreous.
Figure 3B:
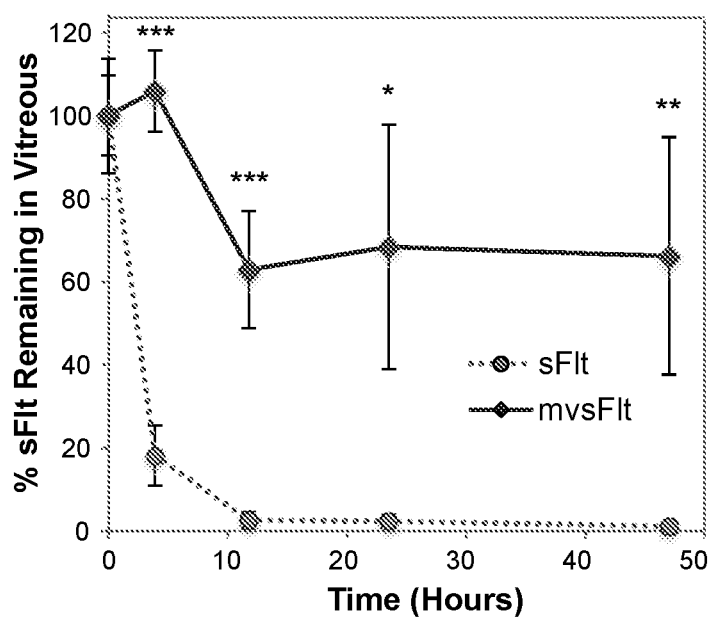

FIG. 3A-3B: mvsFlt has Longer Residence Time in the Rat Vitreous.

A) Schematic depicting methods used to determine the half-life of fluorescently tagged sFlt and mvsFlt in the rat vitreous. The vitreous was injected with 5 µl of Alexa Fluor 488-tagged sFlt or mvsFlt. After 0, 4, 12, 24, and 48 hours, the rats were sacrificed and their eyes were enucleated and frozen for analysis. The vitreous was then removed, immersed in RIPA buffer and homogenized for subsequent fluorescence measurements. B) Conjugation to HyA significantly improves residence time of sFlt in the vitreous after 48 hours in comparison to sFlt. Results are expressed as mean±SD (*p<0.05, p<0.01, *p<0.001). * indicates a difference between the mvsFlt and sFlt at the given time point. Two-way ANOVA gives p-value ***<0.001.

FIG. 6: Higher Molecular Weight Dextran Displays Longer Residence Time In Vivo.

Validation experiment demonstrating the effect of size on the retention of fluorescently tagged dextrans. The 2 MDa dextran (solid line) has significantly improved residence time over the 40 kDa (dashed line) over 48 hours. The half-life of the 40 kDa and the 2 MDa dextrans is 3.2 and 5 hours, respectively. * indicates a difference between the 40 kDa and 2 MDa dextran at the given time point. Two-way ANOVA gives p-value*<0.05 (** corresponds to a P-value less than 0.01).

mvsFlt is a More Potent Inhibitor of Retinal Neovascularization

An OIR model of retinal angiogenesis assay was used to examine the effect of HyA conjugation of sFlt inhibition of retinal angiogenesis. This short-term model allowed indirect examination of the effect of mvsFlt half-life on prolonged angiogenesis inhibition. Neovascular coverage was calculated by comparing the area of vascular coverage to total retinal area. After 5 days of treatment, retinal vascular coverage of PBS-injected eyes was 84.3±3.8% and retinas treated with intravitreal injections of sFlt were 85.4±6.1%. In contrast, retinas from rats treated with intravitreal injections of mvsFlt were significantly lower and had 72.9±3.4% retinal vascular coverage (FIG. 4).

Figure 4A:
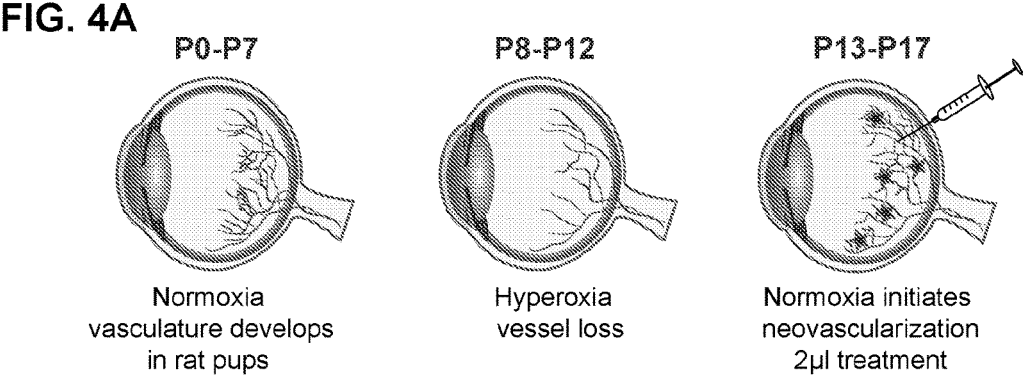
FIG. 4A-4C depict inhibition of retinal angiogenesis by mvsFlt.
Figure 4B:
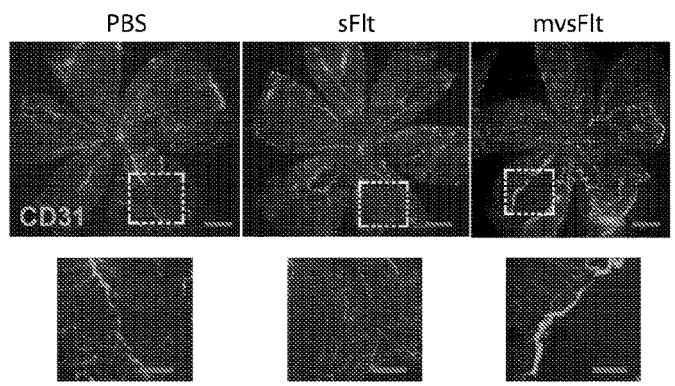
Figure 4C:
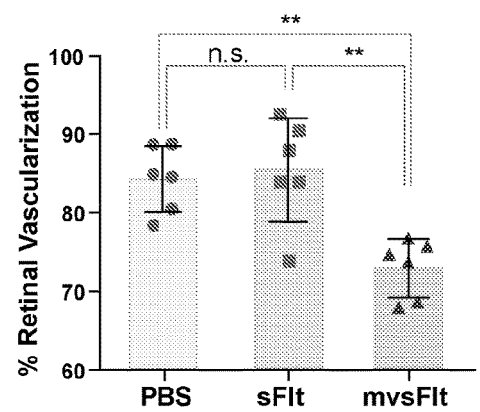

FIG. 4A-4C: mvsFlt Inhibits Retinal Angiogenesis.

A) Schematic showing methods used for carrying out the OIR model. Newborn rat pups were housed in normoxic conditions (21% oxygen, room air) from post-natal day (P) 0-7 to allow for normal retinal vasculature development and then transferred to hyperoxic conditions from P7-P12, which induces vessel pruning. At P13, the pups are transferred back into normoxic conditions and treated with 2 µl of PBS, sFlt or mvsFlt and sacrificed at P17. B) Representative images of retinas treated with PBS, sFlt and mvsFlt. Green staining indicates CD31+ cells. Scale bar corresponds to 250 µm. Dashed boxes magnify that portion of tissue (scale bar corresponds to 100 µm). C) Quantified retinal vascularization after 5 days of treatment. Percent retinal vascularization was calculated by comparing the area of vascularization to the total retinal area in the image. One-way ANOVA gives p-value*<0.001 (n.s.—not significant; p<0.01).

Figure 5A:
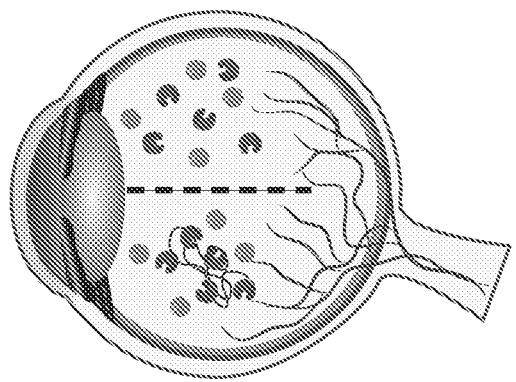
FIG. 5A-5B provide a schematic depiction of a proposed mvsFlt mechanism of action.
Figure 5B:
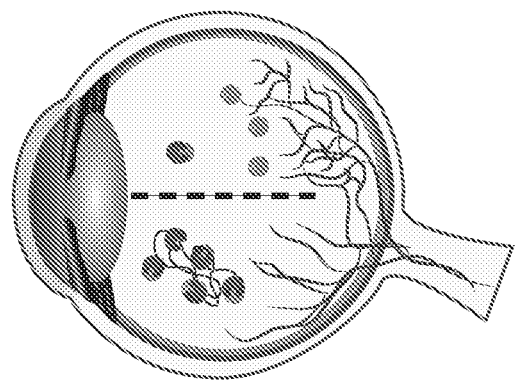

At the time of injection, both sFlt and mvsFlt have similar concentrations in the vitreous (FIG. 5A). Over time, sFlt is small enough to be cleared from the vitreous leaving much lower concentrations of drug (FIG. 5B, top). This allows for an increase in the intravitreal VEGF concentration, which induces angiogenesis. In contrast, mvsFlt has a much longer intravitreal residence time and is thus able to act as a sponge for VEGF over time (FIG. 5B, bottom), inhibiting angiogenesis and maintaining the basal level of vascularization in the retina.

FIG. 5A-5B: Schematic Demonstrating the Proposed Mechanism of mvsFlt Action.

A) sFlt (red, unconjugated) and mvsFlt (red conjugated blue chain of HyA) are injected into a diabetic retina where there is a high concentration of VEGF (green circles). B) After a given time, t, the majority of the sFlt has been cleared from the vitreous and VEGF is thus able to induce blood vessel growth. mvsFlt has a longer residence time in the vitreous and is able to bind and inhibit VEGF over much longer periods of time, leading to prolonged inhibition of retinal angiogenesis.

REFERENCES

1. Shaw J E, Sicree R A, Zimmet P Z. Global estimates of the prevalence of diabetes for 2010 and 2030. Diabetes Res Clin Pract. 2010; 87(1):4-14.
2. Antonetti D A, Klein R, Gardner T W. Diabetic retinopathy. N Engl J Med. 2012 Mar. 29; 366(13):1227-39.
3. Engerman R L. Perspectives in Diabetes Pathogenesis of Diabetic Retinopathy. Diabetes. 1989; 38:1203-6.
4. Fong, D. S., Aiello, L., Gardner, T. W., King, G. L., Blankenship, G., Cavallerano, J. D., Ferris, F. L., Klein R. Retinopathy in Diabetes. Diabetes Care. 2004 Jan. 1; 27:S84-7.
5. Boulton M, Foreman D, Williams G, McLeod D. VEGF localisation in diabetic retinopathy. Br J Ophthalmol. 1998 May; 82(5):561-8.
6. Miller J W, Le Couter J, Strauss E C, Ferrara N. Vascular endothelial growth factor a in intraocular vascular disease. Ophthalmology. Elsevier Inc.; 2013 January; 120 (1):106-14.
7. Witmer A. Vascular endothelial growth factors and angiogenesis in eye disease. Prog Retin Eye Res. 2003 January; 22(1):1-29.
8. Stewart M W, Rosenfeld P J, Penha F M, Wang F, Yehoshua Z, Bueno-Lopez E, et al. Pharmacokinetic rationale for dosing every 2 weeks versus 4 weeks with intravitreal ranibizumab, bevacizumab, and aflibercept (vascular endothelial growth factor Trap-eye). Retina. 2012; 32(3):434-57.
9. Pagliarini S, Beatty S, Lipkova B, Perez-Salvador Garcia E, Reynders S, Gekkieva M, et al. A 2-year, phase IV, multicentre, observational study of ranibizumab 0.5 mg in patients with neovascular age-related macular degeneration in routine clinical practice: The EPICOHORT study. J Ophthalmol. 2014; 2014:1-9.
10. Cohen S Y, Mimoun G, Oubraham H, Zourdani A, Malbrel C, Quere S, et al. Changes in visual acuity in patients with wet age-related macular degeneration treated with intravitreal ranibizumab in daily clinical practice: the LUMIERE study. Retina. 2013; 33(3):474-81.
11. Tanaka K, Yamaguchi S, Sawano A, Shibuya M. Characterization of the extracellular domain in vascular endothelial growth factor receptor-1 (Flt-1 tyrosine kinase). JpnJCancer Res. 1997; 88(9):867-76.
12. Altiok E I, Santiago-Ortiz J L, Zbinden A, Jha A K, Bhatnagar D, Jackson W M, et al. Multivalent Hyaluronic Acid Bioconjugates Improve sFlt Activity In Vitro. (under Rev. 2015;
13. Ma L, Wang X, Zhang Z, Zhou X, Chen A, Yao L. Identification of the ligand-binding domain of human vascular-endothelial-growth-factor receptor Flt-1. Biotechnol Appl Biochem. 2001; 34:199-204.
14. Han B W, Layman H, Rode N A, Conway A, Schaffer D V., Boudreau N, et al. Multivalent conjugates of sonic hedgehog accelerate diabetic wound healing. Tissue Eng Part A. 2015; 21:2366-78.
15. Conway A, Vazin T, Spelke D P, Rode N A, Healy K E, Kane R S, et al. Multivalent ligands control stem cell behaviour in vitro and in vivo. Nat Nanotechnol. Nature Publishing Group; 2013 Oct. 20; 8(October):831-8.
16. Wall S T, Saha K, Ashton R S, Kam K R, Schaffer D V, Healy K E. Multivalency of Sonic hedgehog conjugated to linear polymer chains modulates protein potency. Bioconjug Chem. 2008 April; 19(4):806-12.
17. Smith L E H, Wesolowski E, McLellan A, Kostyk S K, D'Amato R, Sullivan R, et al. Oxygen-induced retinopathy in the mouse. Investig Ophthalmol Vis Sci. 1994; 35(1):101-11.
18. Ito T-K, Ishii G, Saito S, Yano K, Hoshino A, Suzuki T, et al. Degradation of soluble VEGF receptor-1 by MMP-7 allows VEGF access to endothelial cells. Blood. 2009; 113(10):2363-9.
19. Chan M F, Li J, Bertrand A, Casbon A-J, Lin J H, Maltseva I, et al. Protective effects of matrix metalloproteinase-12 following corneal injury. J Cell Sci. 2013; 126(Pt 17):3948-60.
20. Staton C A, Reed M W R, Brown N J. A critical analysis of current in vitro and in vivo angiogenesis assays. Int J Exp Pathol. 2009; 90(3):195-221.
21. Gaudana R, Ananthula H K, Parenky A, Mitra A K. Ocular drug delivery. AAPS J. 2010 September; 12(3): 348-60.
22. Hornof M, Toropainen E, Urtti A. Cell culture models of the ocular barriers. Eur J Pharm Biopharm. 2005; 60(2): 207-25.
23. Urtti A, Salminen L Minimizing Systemic Absorption of Topically Administered Ophtalmic Drugs. Sury Ophtalmol. 1993; 37(6):435-56.
24. Abrishami M, Zarei-Ghanavati S, Soroush D, Rouhbakhsh M, Jaafari M R, Malaekeh-Nikouei B. Preparation, characterization, and in vivo evaluation of nanoliposomes-encapsulated bevacizumab (avastin) for intravitreal administration. Retina. 2009; 29(5):699-703.
25. Drolet D W, Nelson J, Tucker C E, Zack P M, Nixon K, Bolin R, et al. Pharmacokinetics and safety of an anti-vascular endothelial growth factor aptamer (NX1838) following injection into the vitreous humor of rhesus monkeys. Pharm Res. 2000; 17(12):1503-10.
26. Nicholson B P, Schachat A P. A review of clinical trials of anti-VEGF agents for diabetic retinopathy. Graefes Arch Clin Exp Ophthalmol. 2010 July; 248(7):915-30.
27. Ricci B. Oxygen-induced retinopathy in the rat model. Doc Ophthalmol. 1990; 74(3):171-7.
28. Akula J D, Favazza T L, Mocko J A, Benador I Y, Asturias A L, Kleinman M S, et al. The anatomy of the rat eye with oxygen-induced retinopathy. Doc Ophthalmol. 2010; 120(1):41-50.
29. Tan L E, Orilla W, Hughes P M, Tsai S, Burke J A, Wilson C G. Effects of vitreous liquefaction on the intravitreal distribution of sodium fluorescein, fluorescein dextran, and fluorescent microparticles. Invest Ophthalmol Vis Sci. 2011; 52(2):1111-8.
30. Maurice D. Review: practical issues in intravitreal drug delivery. J Ocul Pharmacol Ther. 2001 August; 17(4):393-401.
31. Bakri S J, Snyder M R, Reid J M, Pulido J S, Ezzat M K, Singh R J. Pharmacokinetics of intravitreal ranibizumab (Lucentis). Ophthalmology. 2007 December; 114 (12):2179-82.
32. Gaudreault J, Fei D, Rusit J, Suboc P, Shiu V. Preclinical pharmacokinetics of Ranibizumab (rhuFabV2) after a single intravitreal administration. Invest Ophthalmol Vis Sci. 2005 February; 46(2):726-33.
33. Lee S S, Robinson M R. Novel drug delivery systems for retinal diseases. A review. Ophthalmic Res. 2009 January; 41(3):124-35.

34. Bakri S J, Snyder M R, Reid J M, Pulido J S, Singh R J. Pharmacokinetics of intravitreal bevacizumab (Avastin). Ophthalmology. 2007 May; 114(5):855-9.
35. Moradi A, Sepah Y J, Sadiq M A, Nasir H, Kherani S, Sophie R, et al. Vascular endothelial growth factor trap-eye (Aflibercept) for the management of diabetic macular edema. World J Diabetes. 2013; 4(6):303-9.
36. Stewart M W. What are the half-lives of ranibizumab and aflibercept (VEGF Trap-eye) in human eyes? Calculations with a mathematical model. Eye Reports. 2011 Jun. 9; 1(1):5-7.
37. Kane F E, Burdan J, Cutino A, Green K E. Iluvien: a new sustained delivery technology for posterior eye disease. Expert Opin Drug Deliv. 2008; 5(9):1039-46.
38. Boyer D S, Yoon Y H, Belfort R, Bandello F, Maturi R K, Augustin A J, et al. Three-Year, Randomized, Sham-Controlled Trial of Dexamethasone Intravitreal Implant in Patients with Diabetic Macular Edema. Ophthalmology. 2014;
39. Mohammad D A, Sweet B V, Elner S G. Retisert: is the new advance in treatment of uveitis a good one? Ann Pharmacother. 2007; 41(3):449-54.
40. Bochot A, Fattal E. Liposomes for intravitreal drug delivery: a state of the art. J Control Release. Elsevier B.V.; 2012 Jul. 20; 161(2):628-34.
41. Sahoo S K, Dilnawaz F, Krishnakumar S. Nanotechnology in ocular drug delivery. Drug Discov Today. 2008 February; 13(3-4):144-51.
42. Veronese F M. Peptide and protein PEGylation. Biomaterials. 2001 March; 22(5):405-17.
43. Fishburn S C. The pharmacology of PEGylation: Balancing P D with PK to generate novel therapeutics. J Pharm Sci. 2010; 97(10):4167-83.
44. Ng E W M, Shima D T, Calias P, Cunningham E T, Guyer D R, Adamis A P. Pegaptanib, a targeted anti-VEGF aptamer for ocular vascular disease. Nat Rev Drug Discov. 2006 February; 5(2):123-32.
45. Necas J, Bartosikova L, Brauner P, Kolar J. Hyaluronic acid (hyaluronan): a review. Vet Med. 2008; 2008(8):397-411.

Example 2: Multivalent Hyaluronic Acid Bioconjugates Improve sFlt Activity In Vitro Materials and Methods

Expression of Soluble Flt-1 Receptor

The sFlt sequence for the first 3 Ig-like extracellular domains of sFlt-1 [15] was cloned into the pFastBac1 plasmid (Life Technologies) and then transformed into DH10Bac *E. coli*, which were plated on triple antibiotic plates containing kanamycin (50 μg/mL), gentamicin (7 μg/mL, Sigma Aldrich), tetracycline (10 μg/mL, Sigma Aldrich), IPTG (40 μg/mL, Sigma Aldrich) and Bluo-gal (100 μg/mL, Thermo Fisher Scientific). The sFlt gene-containing bacmid was isolated from DH10Bac *E. coli* (Life Technologies) and transfected into SF9 insect cells for virus production (provided by the Tissue Culture Facility, UC Berkeley). Virus was then used to infect High Five insect cells (provided by the Tissue Culture Facility, UC Berkeley) to induce sFlt protein expression. After 3 days, protein was purified from the supernatant using Ni-NTA agarose beads (Qiagen Laboratories). Recombinant sFlt was eluted from the Ni-NTA beads using an imidazole gradient and then concentrated and buffer exchanged with 10% glycerol/PBS using Amicon Ultra-15 mL Centrifugal devices (EMD Millipore). The protein solution was sterile filtered and the concentration was determined using a BCA assay (Thermo Fisher Scientific).

mvsFlt Conjugate Synthesis

Conjugation of sFlt to HyA was carried out according to the schematic in FIG. 1A, as previously described [16-18]. To make thiol-reactive HyA intermediates, 3,3'-N-(ε-maleimidocaproic acid) hydrazide (EMCH, Thermo Fisher Scientific, 1.2 mg/mL), 1-hydroxybenzotriazole hydrate (HOBt, Sigma Aldrich, 0.3 mg/mL) and 1-ethyl-3-(3-dimethylaminopropyl) carbodiimide hydrochloride (EDC, Thermo Fisher Scientific, 10 mg/mL) were added to a 3 mg/mL solution of HyA (Lifecore Biotechnology) of various molecular weights in 0.1 M 2-(N-morpholino)ethanesulphonic acid (MES) (Sigma Aldrich) buffer (pH 6.5) and allowed to react at 4° C. for 4 hours. The solution was then dialyzed into pH 7.0 PBS containing 10% glycerol. Recombinant sFlt was treated with 2-iminothiolane at 10 molar excess to create thiol groups for conjugation to the maleimide group on EMCH. sFlt was then added to activated HyA-EMCH at 10:1 and 30:1 molar ratios of sFlt to HyA to create the mvsFlt bioconjugates and allowed to react at 4° C. overnight. The mvsFlt reactions were dialyzed exhaustively using 100 kDa molecular weight cut-off (MWCO) Float-A-Lyzer G2 (Spectrum Labs) dialysis tubes in pH 7.0 PBS to remove unreacted sFlt. The BCA assay was used to measure the protein concentrations of the mvsFlt bioconjugates. Conjugates were defined with 10:1 sFlt to HyA molar feed ratios as 'low conjugation ratio' (LCR) mvsFlt and 30:1 molar feed ratios 'high conjugation ratio' (HCR) mvsFlt.

SEC-MALS Characterization of mvsFlt

Protein conjugation was characterized using size exclusion chromatography with multiangle light scattering (SEC-MALS) as previous described [19]. Briefly, the SEC-MALS setup consisted of an Agilent HPLC 1100 with a DAWN-HELEOS II multiangle laser light scattering detector and Optilab relative refractive interferometer (Wyatt Technology, Santa Barbara, Calif.). Refractive index change was measured differentially with 690 nm laser and UV absorbance was measured with the diode array detector at 280 nm. Shodex OH pak SB-804 columns were used for separation (Phenomenex Inc.). Prior to analysis, the mvsFlt conjugates were sterile filtered through a 0.45 μm filter and 200 μL was injected at HyA concentration between 0.2-0.5 mg/mL. The do/dc values were determined using SEC-MALS to be 0.1447 and 0.185 for HyA-EMCH and sFlt, respectively. UV extinction coefficients used for HyA-EMCH and sFlt were also determined on SEC-MALS and were 0.022 and 0.894, respectively. Data analysis was carried out using the Astra software (Wyatt Technologies).

SDS-PAGE Analysis of mvsFlt Samples were prepared with 5×SDS dye loading buffer, 2-mercaptoethanol and boiled for 5 minutes at 95° C. Precast Mini-Protean TGX 4-20% gradient gels (Bio-Rad Laboratories) were run for 90 minutes at 110 volts. Gels were then stained with Bio-Safe Coomassie Stain (Bio-Rad Laboratories) for 2 hours and then imaged using a BioRad Molecular Imager ChemiDoc XRS+. The intensities of protein in the stacking and gradient gel were analyzed using ImageJ to determine the amount of protein that was conjugated versus free unconjugated protein that did not dialyze out of solution following the conjugation reaction.

DLS Size Characterization of mvsFlt

A Brookhaven Goniometer & Laser Light Scattering system (BI-200SM, Brookhaven Instruments Corporation) was used to determine the hydrodynamic diameter of mvsFlt bioconjugates. Each sample was filtered at 0.45 μm and loaded into a 150 μL cuvette (BI-SVC, Brookhaven). Data acquisition was performed at 90 degrees with a 637 nm laser for 2 minutes. Data analysis was carried out with BIC Dynamic light Scattering software (Brookhaven) using the BI-9000AT signal processor. The intensity average particle size was obtained using a non-negative least squares (NNLS) analysis method.

Binding Competition ELISA

The mvsFlt conjugates were analyzed using a $VEGF_{165}$ Quantikine Sandwich ELISA (R&D Systems) to examine the effect of HyA conjugation on sFlt inhibition of $VEGF_{165}$. The assay was carried out according to the manufacturer's instructions. Briefly, $VEGF_{165}$ was added to PBS with varying concentrations of sFlt or mvsFlt. Free $VEGF_{165}$ that bound to the capture antibodies on the plate surface were detected using a horseradish peroxidase conjugated detection antibody and quantified using a spectrophotometer at 450 nm.

HUVEC Endothelial Cell Survival Assay

Human umbilical cord vein endothelial cells (HUVECs) were purchased from ATCC and cultured in EBM-2 media (Lonza) in a humidified incubator at 37° C. and 5% $CO_2$. In order to examine the effect of HyA conjugation on the ability of sFlt to bind and inhibit $VEGF_{165}$ activity in vitro, a survival assay was carried out with HUVECs grown in the presence of $VEGF_{165}$ and mvsFlt conjugates. HUVECs were added to 96 well plates coated with 0.2% gelatin at 10,000 cell/well in M199 media. Cells were grown in 2% FBS and 20 ng/mL $VEGF_{165}$ (R&D Systems) in the presence of sFlt or mvsFlt. 72 hours after plating, the media was aspirated and the cells were washed with PBS prior to freezing for analysis with CyQuant (Life Technologies). Total cell number per well was determined by reading fluorescence at 480 nm excitation and 520 nm emission using a fluorometer (Molecular Devices).

HUVEC Tube Formation Assay

HUVEC tube formation assays were carried out in 96-well plates coated with 80 μL of Matrigel (Corning, N.Y.) and incubated at 37° C. for 1 hour to allow gelation to occur. HUVECs were trypsinized and resuspended in M199 with 2% FBS and 20 ng/mL $VEGF_{165}$ and treated with mvsFlt LCR conjugates. Wells were imaged 18 hours after plating and tube formation was quantified using ImageJ software.

HUVEC Migration Assay

Wells of a 12-well plate were coated with 0.2% gelatin. HUVECs were added at 150,000 cells/well in EBM-2 and allowed to attach and spread overnight. Using a 1 mL pipette tip, crosses were scratched into the confluent layer of HUVECs. The wells were then washed with excess PBS to remove cell debris and media and replaced with media containing $VEGF_{165}$ and mvsFlt. Scratches were imaged at 0 and 24 hours post scratch and the area without cells was quantified using ImageJ and T-scratch software (CSE Laboratory software, ETH Zurich). The percent open wound area was calculated by comparing the open scratch area at 24 hours to the open scratch area at 0 hours.

Retention of mvsFlt in Crosslinked HyA Gels

To model the chemical and network structure of the vitreous, acrylated HyA (AcHyA) hydrogels were synthesized as described previously [20,21]. Briefly, adipic acid dihydrazide (ADH, Sigma Aldrich) was added in 30 molar excess to HyA in deionized water (DI). EDC (3 mmol) and HOBt (3 mmol) were dissolved in DMSO/water and added to the HyA solution. The solution was allowed to react for 24 hours and then dialyzed exhaustively against DI water. HyA-ADH was precipitated in 100% ethanol and reacted with acryloxysuccinimide to generate acrylate groups on the HyA. The resulting AcHyA was exhaustively dialyzed and lyophilized for storage. The presence of grafted acrylate groups on HyA chains was confirmed using $H^1$-NMR.

To make 1% AcHyA hydrogels, 8 mg of AcHyA was dissolved in 800 μL of triethanolamine-buffer (TEOA; 0.3 M, pH 8). Either 5 μg of Alexafluor 488 5-SDP ester (Life Technologies) tagged sFlt, 650 KDa LCR mvsFlt or bovine serum albumin (BSA) were added in 50 μL volumes to the AcHyA solution prior to crosslinking. Thiolated 5 kDa-PEG crosslinker (Laysan Bio, Inc.) was dissolved in 100 μL of TEOA buffer and added to dissolved AcHyA. Cell culture inserts with 4 μm sized pores (Millipore Corporation, Billerica, Minn.) were added to wells of a 24-well plate and 70 μL of gel containing sFlt, mvsFlt or BSA was added to each insert. The gels were allowed to crosslink at 37° C. for 1 hour before adding 150 μL of PBS to the wells and submerging the hydrogels. To determine release kinetics, the well supernatant was collected and fully replaced at 0, 1, 2, 3, 7, 10 and 14 days. Samples were read with a fluorometer to detect the fluorescently tagged sFlt, mvsFlt and BSA in the supernatant.

Fluorescence Recovery after Photobleaching (FRAP) Diffusivity Measurement

FRAP measurements were performed on 1% AcHyA hydrogels containing FITC labeled sFlt and 650 kDa LCR mvsFlt. Total fluorescence intensity of the hydrogels was acquired using a Zeiss LSM710 laser-scanning microscope (Carl Zeiss, Jena, Germany) with a 20× magnification objective and an argon laser set at 488 nm with 50% power. Photobleaching was done by exposing a 100×100-μm spot in the field of view to high intensity laser light. The area was monitored by 15 pre-bleach scanned images at low laser intensity (2%), then bleached to 75% of the starting fluorescence intensity at 100% laser power. A total of about 300 image scans of less than 1 second were collected for each sample. The mobile fraction of fluorescent sFlt and mvsFlt molecules within the hydrogel was determined by comparing the fluorescence in the bleached region after full recovery ($F_\infty$) with the fluorescence before bleaching ($F_{initial}$) and just after bleaching ($F_0$). The mobile fraction R was defined according to equation (1):

$$R = \frac{(F_\infty - F_0)}{(F_{initial} - F_0)} \tag{1}$$

Enzymatic Degradation with MMP-7

Matrix metalloproteinase-7 (MMP-7) has been previously shown to specifically degrade sFlt [22]. To determine whether HyA conjugation shielded mvsFlt from degradation, sFlt and mvsFlt were treated with varying amounts of MMP-7 (EMD Millipore). sFlt and mvsFlt were incubated with matrix metalloproteinase-7 (MMP-7) for 12 hours at 37 C while shaking at high (1:1 molar ratio MMP-7:sFlt), medium (1:2), and low (1:4) molar ratios of MMP-7 to sFlt. The enzyme-treated sFlt and mvsFlt were then loaded into precast Mini-Protean TGX 4-20% gradient gels (Bio-Rad Laboratories) and run at 110 volts for 90 minutes. Gels were then stained using a silver staining kit (Thermo Fisher Scientific) according to the manufacturer's instructions. The degree of enzymatic degradation was assessed by quantifying the total amount of protein remaining in the gel following treatment with MMP-7. Each well was normalized to their respective no-MMP-7 well and background intensity was subtracted according to the blank well between the groups on the gel.

Statistical Analysis

All quantitative experiments were performed in triplicate. Values are expressed as means±standard deviations (SD). One-way ANOVA with Tukey post-hoc analysis was used to compare treatment groups in the quantitative measurements where appropriate and p<0.05 was used to assess statistical significance.

Results

The overall goal of this study was to synthesize protein-polymer bioconjugates to increase the residence time of anti-VEGF drugs in the vitreous for use in treating patients with DR. In contrast to drugs currently used for the treatment of DR that suffer from short half-lives, large multivalent protein bioconjugates with unperturbed affinity for $VEGF_{165}$ and good enzymatic stability were developed, which bioconjugates that show delayed diffusion and mobility in an in vitro model of the vitreous.

FIGS. 7A-7D. Multivalent sFlt Synthesis and Schematics.

A) mvsFlt bioconjugates were synthesized using a 3-step reaction in which HyA was reacted with EDC and EMCH to create a cysteine reactive HyA-EMCH intermediate. sFlt was then treated with 2-iminothiolane and then reacted with the HyA-EMCH intermediate for the synthesis of the final product. B) Schematic of protein conjugation to HyA and subsequent binding to $VEGF_{165}$. The ratio a:b represents the valency of sFlt molecules (a) covalently bound to a single chain of HyA (b). C) Schematic of low conjugation ratio (LCR) mvsFlt conjugates which are synthesized by reacting 10 molecules of sFlt with 1 HyA chain. This reaction has 61% conjugation efficiency as determined by SEC-MALS (see Table 1). D) Schematic of high conjugation ratio (HCR) mvsFlt conjugates which are synthesized by reacting 30 molecules of sFlt with 1 HyA chain (same molecular weight of HyA as in (C)). This reaction has 52% conjugation efficiency as determined by SEC-MALS (see Table 1).

Figure 8A:
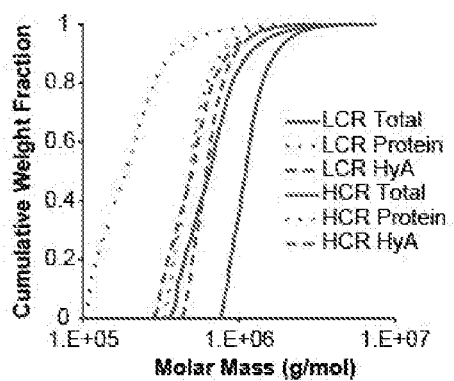
FIG. 8A-8D depict characterization of mvsFlt conjugation efficiency and size.
Figure 8B:
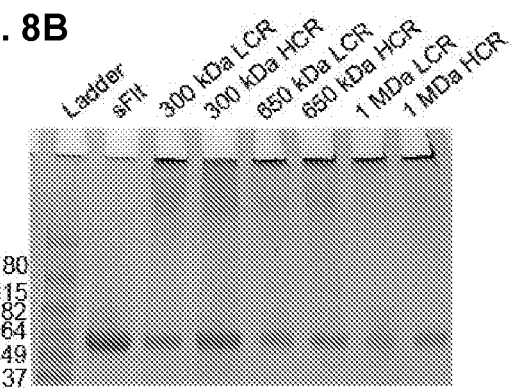
Figure 8C:
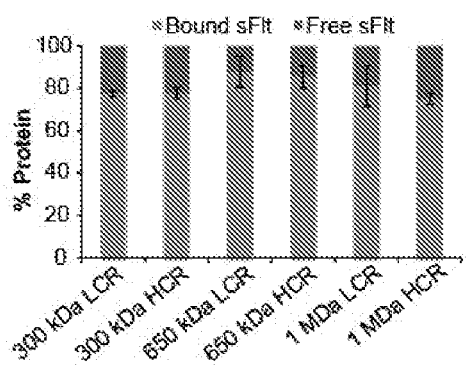

The synthesis of mvsFlt conjugates was carried out according to the schematics shown in FIG. 7A-7D. mvsFlt was created at low (LCR, FIG. 7C) and high (HCR, FIG. 7D) conjugation ratios in order to determine whether a certain valency would provide an enhanced effect on VEGF binding. sFlt was successfully conjugated to HyA at several different molecular weights of HyA and valencies, which were significantly larger than the sFlt in its unconjugated form (FIG. 8A-8D). The molecular weights of the protein and polymer components of the conjugates were characterized using SEC-MALS as shown in Table 1 and FIG. 8A. Conjugates with 10:1 feed ratios (termed low conjugation ratio, LCR) of sFlt to HyA averaged 61.2±12.5% conjugation efficiency whereas conjugates with 30:1 sFlt to HyA feed ratios (termed high conjugation ratio, HCR) had conjugation efficiencies averaging 51.8±4.1%. SDS-PAGE of unbound sFlt exhibited a protein band at the predicted 50 kDa. Conversely, mvsFlt bioconjugates only migrated into the stacking portion of the gel, indicating inhibited mobility as a result of covalent attachment to the much larger multivalent conjugate (FIG. 8B). Gel analysis using ImageJ indicated that on average 76.4±6.7% of sFlt in the mvsFlt bioconjugates was covalently bound whereas the rest of the detected sFlt was presumably non-specifically interacting with the hyaluronic acid chain in solution and thus could not be removed by dialysis (FIG. 8C).

TABLE 1

SEC-MALS analysis of all mvsFlt conjugates.

| | 300 kDa LCR* | 300 kDa HCR+ | 650 kDa LCR* | 650 kDa HCR+ | 1 MDa LCR* | 1 MDa HCR+ |
|---|---|---|---|---|---|---|
| HyA Mn[a] | 2.7E5 | 2.1E5 | 5.9E5 | 6.4E5 | 9.7E5 | 1.0E6 |
| HyA Mw[b] | 3.1E5 | 3.4E5 | 7.1E5 | 7.1E5 | 1.2E6 | 1.1E6 |
| HyA PDI[c] | 1.1 | 1.6 | 1.2 | 1.1 | 1.3 | 1.1 |
| sFlt:HyA[d] | 7.9 | 15.4 | 5.3 | 17.1 | 5.2 | 14.1 |

[a]Number average molecular weight given in g/mol.
[b]Weight average molecular weight given in g/mol
[c]Polydispersity index given as Mw/Mn
[d]Final stoichiometric ratio of sFlt to HyA calculated by dividing total attached protein Mw by sFlt MW (50 kDa)
*LCR is low conjugation ratio conjugates (10:1 sFlt per HyA chain feed ratio)
+HCR is high conjugation ratio conjugates (30:1 sFlt per HyA chain feed ratio)

Figure 8D:
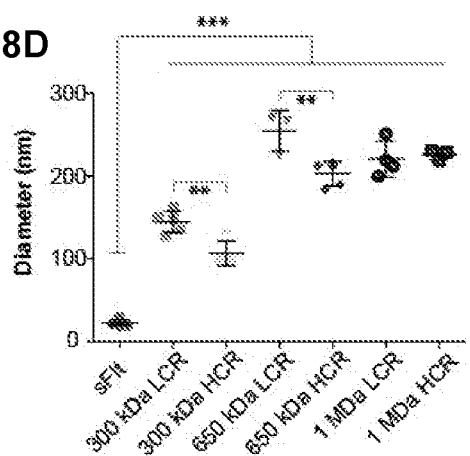

All mvsFlt conjugates were also characterized by DLS to determine conjugate hydrodynamic diameter in solution, as drug size is a critical factor that determines its mobility through biological hydrogels such as the vitreous. Unconjugated sFlt had a diameter of 22.6 nm±3.1 nm whereas mvsFlt conjugates made with HyA of molecular weights of 300 kDa, 650 kDa, and 1 MDa had diameters of 123.9±23.1 nm, 236.3±38.7 nm, and 223±13.9 nm, respectively (FIG. 8D). The size of the mvsFlt conjugates was dependent on the HyA molecular weight for the 300 and 650 kDa conjugates; however, there was no significant difference between the 650 kDa and 1 MDa conjugates (FIG. 8D). Interestingly, HCR conjugates of 300 and 650 kDa molecular weight had lower diameters than their respective LCR conjugates, which could be due to increased positive charge from sFlt on the negatively charged HyA backbone with increasing sFlt attachment causing the conjugate to fold in tighter around itself.

FIG. 8A-8D. Characterizing mvsFlt Conjugation Efficiency and Size.

A) SEC-MALS chromatogram depicting cumulative weight fraction versus molar mass of 650 kDa LCR and HCR bioconjugates. Dotted line, dashed line and solid line represent total molar mass of all covalently attached sFlt proteins, HyA molar mass and total bioconjugate molar mass (all given as g/mol), respectively. B) 4-20% SDS-page gradient gel of sFlt and mvsFlt. Protein bands in the stacking gel indicate successful protein conjugation to HyA. Protein bands within gel represent the proportion of protein that was not covalently bound, but remained in solution after dialysis. C) Quantified protein band intensities of SDS-PAGE gel. Percent bound sFlt was determined by dividing the intensity of protein in the stacking gel by total protein intensity within the respective well. Free sFlt was determined by dividing the intensity of protein within the separating gel by the total protein intensity within the respective well. D) Dynamic light scattering analysis of conjugates. sFlt was significantly smaller than all mvsFlt bioconjugates (*p<0.001). In the case of 300 and 650 kDa mvsFlt bioconjugates, the LCR mvsFlt was significantly larger than its respective HCR conjugate (p<0.01). Values are given as ±SD.

Figure 9A:
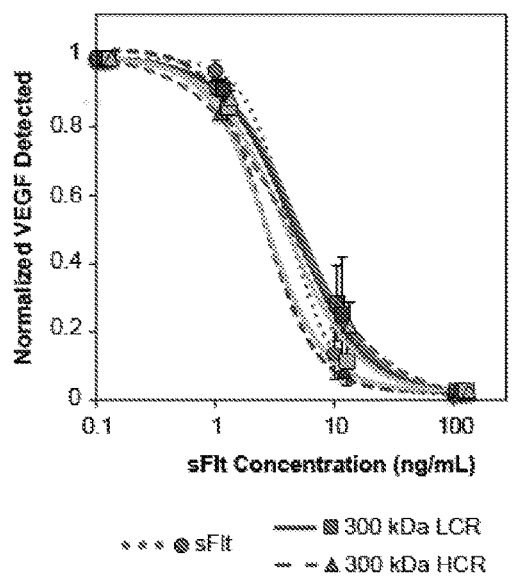
FIG. 9A-9B depict the effect of mvsFlt bioconjugates on $VEGF_{165}$-dependent activities in $VEGF_{165}$ ELISA and $VEGF_{165}$-dependent HUVEC survival assays.
Figure 9B:
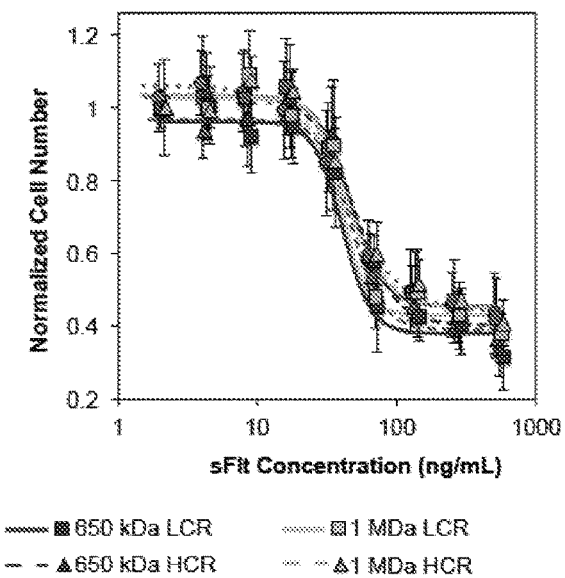
Figure 10A:
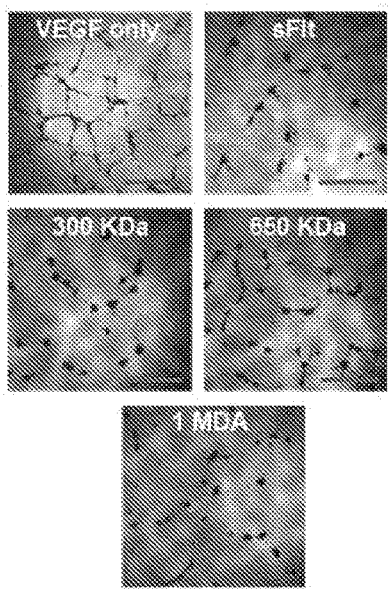
FIG. 10A-10E depict the effect of mvsFlt on HUVEC tube formation.
Figure 10B:
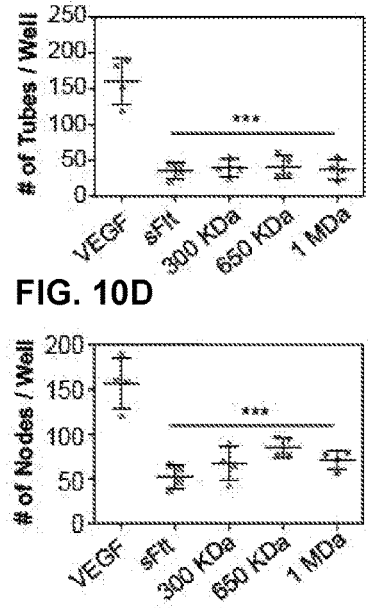
Figure 10C:
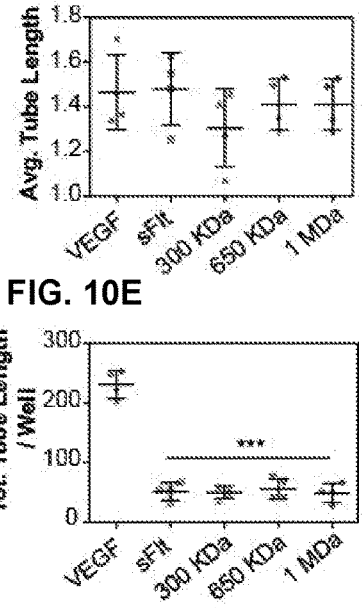
Figure 10D:
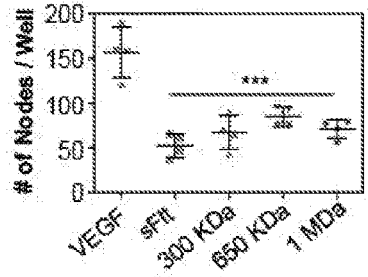
Figure 10E:
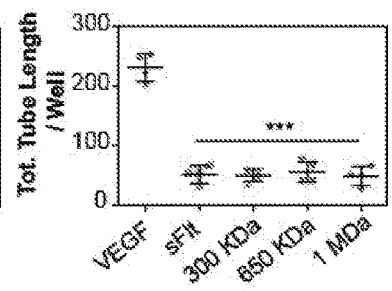

FIG. 9A-9B. All mvsFlt Bioconjugates Maintain their Ability to Inhibit $VEGF_{165}$ Dependent Activities in $VEGF_{165}$ ELISA and $VEGF_{165}$-Dependent HUVEC Survival Assays.

A) Dose-dependent inhibition of $VEGF_{165}$ binding to a capture antibody by mvsFlt bioconjugates. Inhibition was independent of whether the sFlt was bound to HyA or free in solution. There were no significant differences between any of the groups (Table 2). B) Dose-dependent inhibition of HUVEC survival with mvsFlt at different molecular weights and protein valencies in the presence of VEGF$_{165}$. Inhibition was independent of whether the sFlt was bound to HyA or free in solution (Table 2). Values are given as means±SD.

TABLE 2

IC$_{50}$ values from ELISA and HUVEC survival assays examining mvsFlt inhibition of VEGF$_{165}$

|  | ELISA (ng/mL) | HUVEC Survival (ng/mL) |
|---|---|---|
| sFlt unconjugated | 3.8 ± 2.4 | 39.3 ± 4.4 |
| 300 kDa LCR | 4.5 ± 1.5 | 46.9 ± 9.9 |
| 300 kDa HCR | 4.7 ± 1.7 | 44.4 ± 2.6 |
| 650 kDa LCR | 3.9 ± 2.6 | 41.7 ± 6.7 |
| 650 kDa HCR | 2.0 ± 0.1 | 43.2 ± 13.6 |
| 1 MDa LCR | 2.2 ± 0.1 | 44.9 ± 10.7 |
| 1 MDa HCR | 3.3 ± 1.6 | 45.4 ± 2.2 |

Several different assays were employed to determine whether conjugation of sFlt to HyA affected sFlt affinity VEGF$_{165}$ and alter VEGF$_{165}$-dependent cell function. Using a VEGF$_{165}$ specific ELISA a dose-dependent response was observed; the response indicated conjugation of sFlt to HyA did not alter the ability of mvsFlt to bind VEGF$_{165}$ (FIG. 9A). ELISA results indicated that the IC$_{50}$ value of sFlt was 3.8±2.4 ng/mL and the IC$_{50}$ value of the various mvsFlt conjugates averaged to 3.4±1.1 ng/mL (Table 2).

FIG. 10A-10E. mvsFlt Inhibits HUVEC Tube Formation.

A) Representative images of inhibited HUVEC tube formation on Matrigel (BD Biosciences) when treated with 1 µg/mL of all LCR mvsFlt bioconjugates. Cells were seeded at 20,000 cells per well of a 96-well plate on 100 µL of matrigel and imaged at 18 hours. Scale bar=500 µm. B-E) Quantification of total number of tubes per well (B), average tube length (C), total number of nodes (branching points, D), and total tube length per well (E) (***p<0.001).

In survival assays with HUVECs, mvsFlt demonstrated a dose-dependent decrease in survival, and the effect was independent of conjugation to HyA similar to the ELISA results (FIG. 9B, Table 2). These results indicate that covalent conjugation of sFlt to HyA does not reduce the ability of sFlt to bind VEGF. This is extremely promising due to the fact that other conjugation technologies such as PEGylation, have previously reported that conjugation significantly reduces the bioactivity of the protein [23,24].

For subsequent studies, only the LCR conjugates of different molecular weights were studied, since all conjugates performed equally well when examining in vitro VEGF$_{165}$ inhibitory activity in ELISA and survival assays. In vitro tube formation and migration assays enabled examination of the effect of mvsFlt conjugates in vitro on two additional processes involved in angiogenesis in vivo, organization into tubes and cell migration. Similar to the survival data, sFlt and mvsFlt had similar inhibition profiles of VEGF$_{165}$ in these two assays where addition of sFlt and mvsFlt equally inhibited organization into tubes (FIG. 10A-10E) and closure of wounds (FIG. 11A-11B). Taken together, the ELISA and in vitro angiogenesis assays indicated that conjugation of sFlt to HyA did not affect the ability of sFlt to bind VEGF$_{165}$ and that all mvsFlt conjugates maintained their ability to inhibit endothelial cell functions mediated by VEGF$_{165}$ signaling.

FIG. 11A-11B. mvsFlt Inhibits VEGF$_{165}$-Driven HUVEC Migration.

Representative images of inhibition of HUVEC migration with LCR mvsFlt bioconjugates of varying molecular weights. HUVECs were allowed to grow to confluence in 12-well plates prior to making a scratch and were treated with 20 ng/mL VEGF$_{165}$ in the presence of 200 ng/mL mvsFlt. Cells were stained with CellTracker Green (Life Technologies) prior to seeding. Scale bar=20 µm. B) Quantified HUVEC migration following treatment with LCR mvsFlt showing percent open wound area calculated by comparing open wound area at 24 hours to open wound area at time 0 (***p<0.001).

Figure 14A:
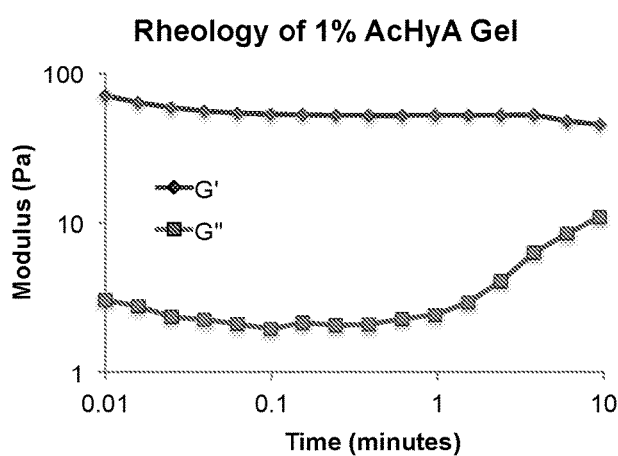
FIG. 14A-14B depict characterization of a HyA hydrogel.
Figure 14B:
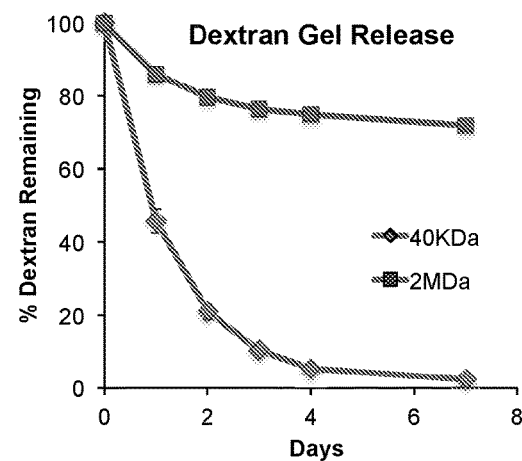
Figure 15A:
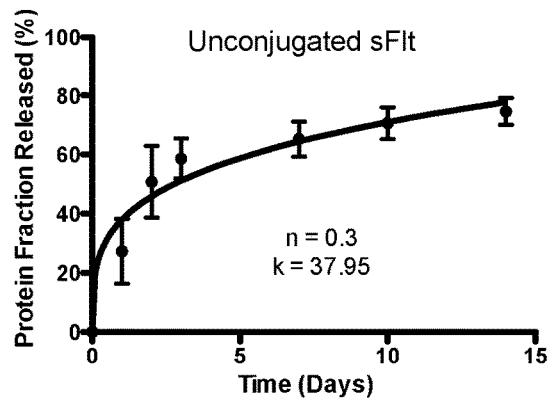
FIG. 15A-15E depict fits for data from gel release data to Fickian diffusion.
Figure 15B:
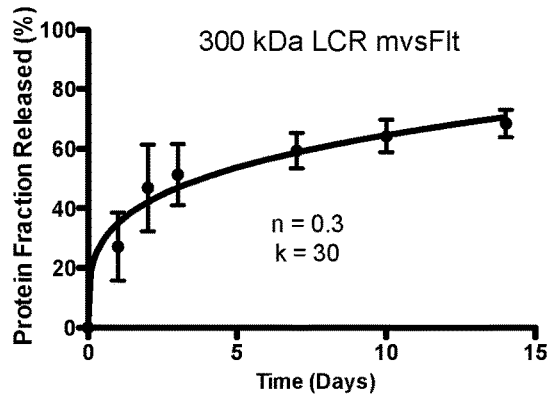
Figure 15C:
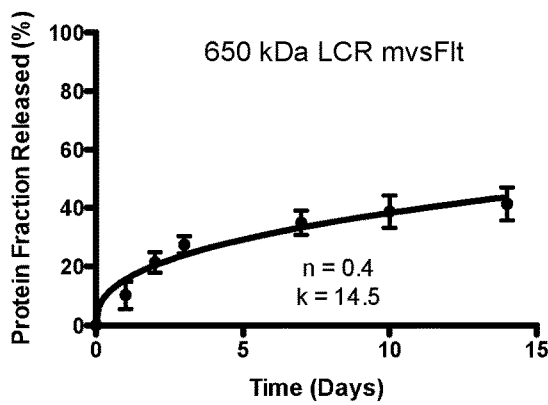
Figure 15D:
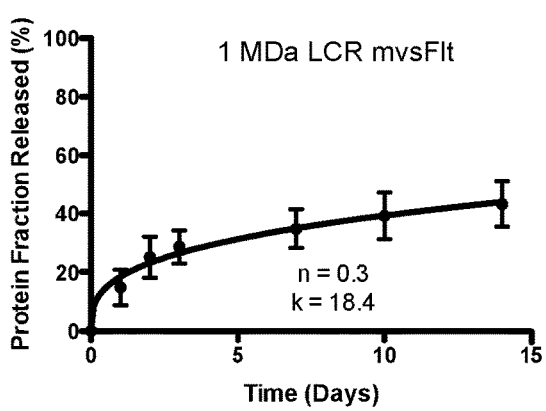
Figure 15E:
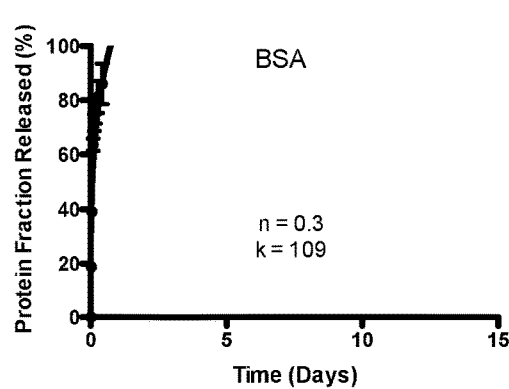

Crosslinked HyA gels [20,21] were used to examine how diffusion conjugation of sFlt to HyA affects diffusion. This hydrogel was chosen as a model system for studying the vitreous in vitro based primarily on compositional similarity to the vitreous with respect to high HyA content. The stiffness of the HyA hydrogel (FIG. 14A) was higher than published reports examining bovine and porcine vitreous stiffness [25], suggesting the predictions of drug clearance from the vitreous using this model may not be sufficient to estimate actual in vivo rates. However, it is anticipated that the diffusion of sFlt and mvsFlt through these gels will be instructive to predict the benefits of conjugation to HyA given the compositional similarities of the model with the vitreous. Several different models were used to characterize the mesh size of HyA hydrogels (Table 3). Preliminary experiments analyzing size dependent diffusion using 40 kDa and 2 MDa fluorescently tagged dextrans (Life Technologies) were used to confirm that this hydrogel system would be appropriate for examining molecular weight and size dependent diffusion (FIG. 14B). Using this system, the release kinetics of sFlt and all LCR mvsFlt bioconjugates from the HyA gels were analyzed. It was expected that the main effect of mvsFlt bioconjugates would be size-dependent decreases in mobility. Only conjugates of varying sizes were analyzed, while holding valency constant. After 14 days, only 30.8±1.9% of sFlt remained in the gel in comparison to 38.3%±2.2%, 63.8±0.5% and 62.8%±0.4% of 300 kDa, 650 kDa, and 1 MDa LCR conjugates, respectively (FIG. 12A). In comparison, 100% of BSA released after 24 hours, a difference more likely due to significantly different isoelectric points (5.4 for BSA [26] and 9.5 for sFlt [27]) and very low protein affinity for HyA rather than protein size since BSA and sFlt have similar molecular weights.

TABLE 3

$\overline{M}_c$ and mesh size calculations based on swelling and rheological data.

| Model | $\overline{M}_c$ (g/mol)* | ξ (nm)+ |
|---|---|---|
| Peppas/Merrill [28] - Affine (Q)$^a$ | 299,030 | 377 |
| Erman [29] - Phantom (Q)$^a$ | 388,940 | 430 |
| Mooney [30] - Affine (G')$^b$ | 247,750 | 343 |
| Erman [29] - Phantom (G')$^b$ | 123,880 | 242 |

*$\overline{M}_c$ - molecular weight between crosslinks
+ξ - mesh size of 1% HyA gel calculated according to [31]
$^a\overline{M}_c$ calculated from mass swelling data
$^b\overline{M}_c$ calculated from rheology data

FIG. 12A-12C.

sFlt conjugation to HyA decreases mvsFlt mobility and diffusion in HyA gels. A) Alexafluor 488-tagged LCR mvsFlt bioconjugates 650 kDa and 1 MDa encapsulated in 1% HyA hydrogels diffused out significantly slower than unconjugated sFlt and 300 kDa mvsFlt after day 1 (*p<0.05) and persisted until the last time point, day 14 (***p<0.001). B) Representative confocal images corresponding to FRAP experiment of FITC tagged 650 kDa LCR mvsFlt. F$_{initial}$ depicts mvsFlt in the gel prior to bleaching. F$_0$ is the fluorescence measurement immediately after 75% photobleaching; $F_\infty$ corresponds to the maximal recovery of fluorescence at the end of the experiment. C) Normalized fluorescence recovery [f(t)] of FITC labeled sFlt and 650 kDa LCR mvsFlt after photobleaching.

FIG. 14A-14B.

Characterizing the HyA hydrogel. (A) Rheological properties of the 1% HyA hydrogel. (B) Fluorescently tagged 40 kDa dextran encapsulated in HyA hydrogels diffused out significantly faster than the 2 MDa dextran after 7 days (***p<0.001).

To assess whether diffusion through the gel was Fickian, the curves in FIG. 12A were fit using equation (2) as described by Ritger et al. [32]:

$$\frac{M_t}{M_\infty} = kt^n \quad (2)$$

The diffusional exponent, n, is indicative of whether diffusion is Fickian and if n is equal to 0.5, the transport is Fickian. The n value for BSA, sFlt and mvsFlt release was determined to be 0.3-0.4 (FIG. 15A-E), indicating that the diffusion through the gel is not Fickian. BSA was depleted from the gel through rapid burst release due to the extremely small size of the protein and very low affinity to the HyA hydrogel due to charge repulsion, leading to non-Fickian diffusion. The sFlt and mvsFlt conjugates release slower in comparison due in part to ionic affinity with the HyA hydrogel and size. Although the sFlt and BSA are similar in size (50 kDa and 66 kDa, respectively), the sFlt has a much stronger ionic interaction with the matrix, which slows its diffusion from the gel, also resulting in non-Fickian diffusion due to this strong affinity. The 300 kDa mvsFlt conjugate is small enough in size (<150 nm, see FIG. 8D) relative to the estimated hydrogel $\xi$ (Table 3) to release as rapidly as sFlt. The two largest conjugates were close to the mesh size in diameter (>225 nm) and were significantly impeded in their release due to size, resulting in gel release that followed the reptation mechanism of diffusion [33].

Based on data from the sFlt release studies, only the 650 kDa LCR bioconjugate was studied, using FRAP, since this conjugate displayed the highest difference in gel retention in comparison to unconjugated sFlt. The mobile fraction of sFlt in the gel was 73.8±4.4% whereas the mobile fraction of the mvsFlt within the gel was 48.3±3.0%, indicating that a significant portion of the mvsFlt bioconjugate was large enough to become immobile within the gel due to the similarity in diameter between the mvsFlt and the mesh size of the HyA gel. Experimental data in FIG. 12C was fit according to Soumpasis [34] to obtain characteristic diffusion times. Interestingly, the characteristic diffusion time for mvsFlt (94.8±19.5 s) was significantly faster than sFlt (176±18.1 s). This difference may be due to ionic shielding of the positively charged sFlt by the negatively charged hyaluronic acid within the multivalent conjugate, which reduces the overall affinity of the conjugate for the gel allowing for faster diffusion. In contrast, the unconjugated sFlt remains highly positively charged resulting in stronger ionic affinity within the HyA gel that slow its characteristic diffusion time. The mvsFlt in the hydrogel also recovered fluorescence to a significantly lower degree, 85.3±0.8%, in comparison to sFlt, which recovered to 91.6%±2.4%. Although the mvsFlt conjugate displayed faster diffusion, a much smaller percentage of the mvsFlt bioconjugate is actually mobile and the size significantly limited the total fluorescence recovery, results that are also supported by the gel release data in FIG. 12A. It becomes clear that even though mvsFlt can diffuse faster as shown by FRAP in FIG. 12B,C a much smaller portion of this sample is able to move due to size and thus much less of it is released over time as evidenced by the gel release data in FIG. 12A. Taken together, it is anticipated that the effect of size will be the strongest determinant of mvsFlt residence time in vivo.

Figure 13A:
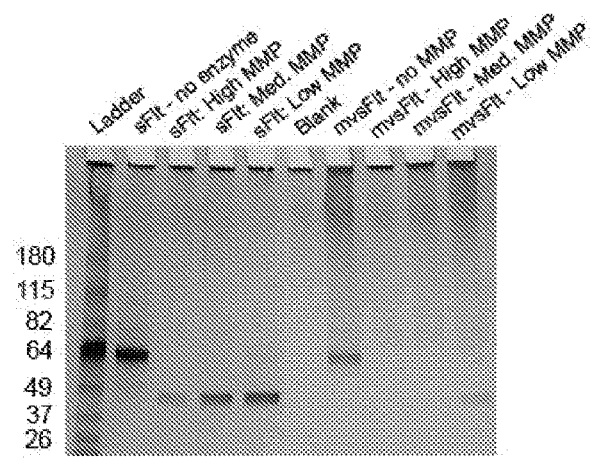
FIG. 13A-13B depict data showing that conjugation to HyA reduces susceptibility to protease degradation by MMP-7.
Figure 13B:
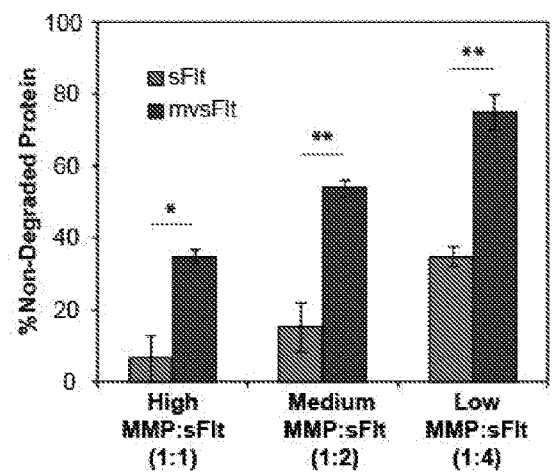

FIG. 13A-13B. Conjugation to HyA Reduces Susceptibility to Protease Degradation by MMP-7.

A) 4-20% SDS-page gradient gel of sFlt and mvsFlt (650 kDa LCR) following 12 hour treatment with MMP-7 at high, medium and low molar ratios of MMP-7 to sFlt, which correspond to 1:1, 1:2 and 1:4 molar ratios of MMP-7 to sFlt. Band intensity was normalized to the no MMP-7 treatment within each group and background was subtracted from each sample using the blank well. B) Quantification of 4-20% gradient gel of sFlt and mvsFlt treated with MMP-7 at high, medium, and low molar ratios of sFlt to MMP-7 for 12 hours (*p<0.05; **p<0.01).

FIG. 15A-15E.

Fits for data from gel release data to examine Fickian diffusion. (A-E) Graphs of fits made with Ritger et al. [13] equation (2) to determine the diffusional exponent, n, and the constant for characteristics of the macromolecular network system and the drug, k.

The effect of conjugation of sFlt to HyA on protease degradation of the sFlt protein was studied using MMP-7, a protease that has been shown to specifically degrade sFlt [22]. It was found that conjugation of sFlt to HyA shielded the degradation of sFlt at all molar ratios of MMP-7 to sFlt (FIG. 13A). At high concentrations of protease (1:1 molar ratio of MMP-7 to sFlt), only 6.8±6.6% of sFlt remained detectable in comparison to 34.8±1.8% of mvsFlt (FIG. 13B). Decreasing the ratio of MMP-7 to sFlt from 1:1 to 1:4 still resulted in significant degradation of sFlt and degradation shielding of the conjugated form, where detectable sFlt increased to 34±2.7% in comparison to detectable mvsFlt at 74.8±4.9% (FIG. 3B). It is believed that the shielding effect of HyA provides for maintaining mvsFlt stability and bioavailability in vivo, aiding in the prolonged anti-angiogenic effect of mvsFlt bioconjugates.

REFERENCES

[1] R. Fong, D. S., Aiello, L., Gardner, T. W., King, G. L., Blankenship, G., Cavallerano, J. D., Ferris, F. L., Klein, Retinopathy in Diabetes, Diabetes Care. 27 (2004) S84-87. doi:10.2337/diacare.27.2007. S84.

[2] M. Boulton, D. Foreman, G. Williams, D. McLeod, VEGF localisation in diabetic retinopathy., Br. J. Ophthalmol. 82 (1998) 561-8. doi:10.1136/bjo.82.5.561.

[3] J. W. Miller, J. Le Couter, E. C. Strauss, N. Ferrara, Vascular endothelial growth factor a in intraocular vascular disease., Ophthalmology. 120 (2013) 106-14. doi: 10.1016/j.ophtha.2012.07.038.

[4] A. Witmer, Vascular endothelial growth factors and angiogenesis in eye disease, Prog. Retin. Eye Res. 22 (2003) 1-29. doi:10.1016/S1350-9462(02)00043-5.

[5] D. a Antonetti, R. Klein, T. W. Gardner, Diabetic retinopathy., N. Engl. J. Med. 366 (2012) 1227-39. doi: 10.1056/NEJMra1005073.

[6] J. G. F. Dowler, Laser management of diabetic retinopathy., J. R. Soc. Med. 96 (2003) 277-279. doi:10.1258/jrsm.96.6.277.

[7] K. a M. Solaiman, M. M. Diab, S. a Dabour, Repeated intravitreal bevacizumab injection with and without macular grid photocoagulation for treatment of diffuse diabetic macular edema., Retina. 33 (2013) 1623-9. doi:10.1097/IAE.0b013e318285c99d.

[8] P. L. Lip, F. Belgore, A. D. Blann, M. W. Hope-Ross, J. M. Gibson, G. Y. H. Lip, Plasma VEGF and soluble VEGF receptor FLT-1 in proliferative retinopathy: Relationship to endothelial dysfunction and laser treatment, Investig. Ophthalmol. Vis. Sci. 41 (2000) 2115-2119.

[9] Q. D. Nguyen, D. M. Brown, D. M. Marcus, D. S. Boyer, S. Patel, L. Feiner, et al., Ranibizumab for diabetic macular edema: Results from 2 phase iii randomized trials: RISE and RIDE, Ophthalmology. 119 (2012) 789-801. doi:10.1016/j.ophtha.2011.12.039.

[10] D.R.C.R. Network, A Phase II Randomized Clinical Trial of Intravitreal Bevacizumab for Diabetic Macular Edema, Ophthalmology. 114 (2007) 1860-1867. doi:10.1016/j.ophtha.2007.05.062.

[11] D. V. Do, Q. D. Nguyen, D. Boyer, U. Schmidt-Erfurth, D. M. Brown, R. Vitti, et al., One-year outcomes of the da VINCI study of VEGF trap-eye in eyes with diabetic macular edema, Ophthalmology. 119 (2012) 1658-1665. doi:10.1016/j.ophtha.2012.02.010.

[12] S. Pagliarini, S. Beatty, B. Lipkova, E. Perez-Salvador Garcia, S. Reynders, M. Gekkieva, et al., A 2-year, phase IV, multicentre, observational study of ranibizumab 0.5 mg in patients with neovascular age-related macular degeneration in routine clinical practice: The EPICOHORT study, J. Ophthalmol. 2014 (2014). doi:10.1155/2014/857148.

[13] S. Y. Cohen, G. Mimoun, H. Oubraham, A. Zourdani, C. Malbrel, S. Quere, et al., Changes in visual acuity in patients with wet age-related macular degeneration treated with intravitreal ranibizumab in daily clinical practice: the LUMIERE study, RETINA. 33 (2013) 474-481. doi:10.1097/IAE.0b013e31827b6324.

[14] J. E. Scott, The chemical morphology of the vitreous., Eye (Lond). 6 (Pt 6) (1992) 553-5. doi:10.1038/eye.1992.120.

[15] L. Ma, X. Wang, Z. Zhang, X. Zhou, a Chen, L. Yao, Identification of the ligand-binding domain of human vascular-endothelial-growth-factor receptor Flt-1., Biotechnol. Appl. Biochem. 34 (2001) 199-204. doi:10.1042/BA20010043.

[16] S. T. Wall, K. Saha, R. S. Ashton, K. R. Kam, D. V Schaffer, K. E. Healy, Multivalency of Sonic hedgehog conjugated to linear polymer chains modulates protein potency., Bioconjug. Chem. 19 (2008) 806-12. doi:10.1021/bc700265k.

[17] A. Conway, T. Vazin, D. P. Spelke, N. a Rode, K. E. Healy, R. S. Kane, et al., Multivalent ligands control stem cell behaviour in vitro and in vivo., Nat. Nanotechnol. (2013) 1-8. doi:10.1038/nnano 2013.205.

[18] B. W. Han, H. Layman, N. A. Rode, A. Conway, D. V Schaffer, N. Boudreau, et al., Multivalent conjugates of sonic hedgehog accelerate diabetic wound healing., Tissue Eng. Part A. 21 (2015) 2366-2378. doi:10.1089/ten.TEA.2014.0281.

[19] J. F. Pollock, R. S. Ashton, N. a Rode, D. V Schaffer, K. E. Healy, Molecular characterization of multivalent bioconjugates by size-exclusion chromatography with multiangle laser light scattering., Bioconjug. Chem. 23 (2012) 1794-801. doi:10.1021/bc3000595.

[20] A. K. Jha, A. Mathur, F. L. Svedlund, J. Ye, Y. Yeghiazarians, K. E. Healy, Molecular Weight and Concentration of Heparin in Hyaluronic Acid-based Matrices Modulates Growth Factor Retention Kinetics and Stem Cell Fate, J. Control. Release. 209 (2015) 308-316. doi:10.1016/j.jconrel.2015.04.034.

[21] A. Jha, K. Tharp, J. Ye, J. Santiago-Ortiz, W. Jackson, A. Stahl, et al., Growth factor sequestering and presenting hydrogels promote survival and engraftment of transplanted stem cells, Biomaterials. 47 (2015) 1-12. doi:10.1016/j.biomaterials.2014.12.043.

[22] T.-K. Ito, G. Ishii, S. Saito, K. Yano, A. Hoshino, T. Suzuki, et al., Degradation of soluble VEGF receptor-1 by MMP-7 allows VEGF access to endothelial cells., Blood. 113 (2009) 2363-9. doi:10.1182/blood-2008-08-172742.

[23] F. M. Veronese, Peptide and protein PEGylation, Biomaterials. 22 (2001) 405-417. doi:10.1016/50142-9612(00)00193-9.

[24] S. C. Fishburn, The pharmacology of PEGylation: Balancing P D with PK to generate novel therapeutics, J. Pharm. Sci. 97 (2010) 4167-4183. doi:10.1002/jps.

[25] C. S. Nickerson, J. Park, J. a Kornfield, H. Karageozian, Rheological properties of the vitreous and the role of hyaluronic acid., J. Biomech. 41 (2008) 1840-6. doi:10.1016/j.jbiomech.2008.04.015.

[26] J. Lu, T. Su, R. Thomas, Structural Conformation of Bovine Serum Albumin Layers at the Air-Water Interface Studied by Neutron Reflection., J. Colloid Interface Sci. 213 (1999) 426-437. doi:10.1006/jcis.1999.6157.

[27] R. Thadhani, T. Kisner, H. Hagmann, V. Bossung, S. Noack, W. Schaarschmidt, et al., Pilot Study of Extracorporeal Removal of Soluble Fms-Like Tyrosine Kinase 1 in Preeclampsia, Circulation. 124 (2011) 940-950. doi:10.1161/CIRCULATIONAHA.111.034793.

[28] N. a. Peppas, E. W. Merrill, Crosslinked poly(vinyl alcohol) hydrogels as swollen elastic networks., J. Appl. Polym. Sci. 21 (1977) 1763-1770. doi:10.1002/app.1977.070210704.

[29] J. E. Mark, B. Erman, Rubberlike Elasticity: A Molecular Primer, 1st ed., John Wiley & Sons, Toronto, 1988.

[30] K. Y. Lee, J. a. Rowley, P. Eiselt, E. M. Moy, K. H. Bouhadir, D. J. Mooney, Controlling mechanical and swelling properties of alginate hydrogels independently by cross-linker type and cross-linking density, Macromolecules. 33 (2000) 4291-4294. doi:10.1021/ma9921347.

[31] J. Baier Leach, K. a. Bivens, C. W. Patrick Jr., C. E. Schmidt, Photocrosslinked hyaluronic acid hydrogels: Natural, biodegradable tissue engineering scaffolds, Biotechnol. Bioeng. 82 (2003) 578-589. doi:10.1002/bit.10605.

[32] P. L. Ritger, N. a. Peppas, A simple equation for description of solute release I. Fickian and non-Fickian release from non-swellable devices in the form of slabs, spheres, cylinders or discs, J. Control. Release. 5 (1987) 23-36. doi:10.1016/0168-3659(87)90035-6.

[33] P. G. De Gennes, Conjectures on the transport of a melt through a gel, Macromolecules. 19 (1986) 1245-1249. doi:10.1021/ma00158a051.

[34] D. M. Soumpasis, Theoretical analysis of fluorescence photobleaching recovery experiments, Biophys. J. 41 (1983) 95-97. doi:10.1016/50006-3495(83)84410-5.

[35] R. Gaudana, H. K. Ananthula, A. Parenky, A. K. Mitra, Ocular drug delivery., AAPS J. 12 (2010) 348-60. doi:10.1208/s12248-010-9183-3.

[36] S. S. Lee, M. R. Robinson, Novel drug delivery systems for retinal diseases. A review., Ophthalmic Res. 41 (2009) 124-35. doi:10.1159/000209665.

[37] H. F. Edelhauser, C. L. Rowe-Rendleman, M. R. Robinson, D. G. Dawson, G. J. Chader, H. E. Grossniklaus, et al., Ophthalmic drug delivery systems for the treatment of retinal diseases: basic research to clinical applications., Invest. Ophthalmol. Vis. Sci. 51 (2010) 5403-5420. doi:10.1167/iovs.10-5392.

[38] E. M. Del Amo, A. Urtti, Current and future ophthalmic drug delivery systems. A shift to the posterior segment., Drug Discov. Today. 13 (2008) 135-43. doi:10.1016/j.drudis.2007.11.002.

[39] T. R. Thrimawithana, S. Young, C. R. Bunt, C. Green, R. G. Alany, Drug delivery to the posterior segment of the eye., Drug Discov. Today. 16 (2011) 270-7. doi:10.1016/j.drudis.2010.12.004.

[40] S. K. Sahoo, F. Dilnawaz, S. Krishnakumar, Nanotechnology in ocular drug delivery., Drug Discov. Today. 13 (2008) 144-51. doi:10.1016/j.drudis.2007.10.021.

[41] D. Maurice, Review: practical issues in intravitreal drug delivery., J. Ocul. Pharmacol. Ther. 17 (2001) 393-401. doi:10.1089/108076801753162807.

[42] R. D. Jager, L. P. Aiello, S. C. Patel, E. T. Cunningham, Risks of intravitreous injection: a comprehensive review., Retina. 24 (2004) 676-698. doi:10.1097/00006982-200410000-00002.

[43] E. J. Oh, J. S. Choi, H. Kim, C K Joo, S. K. Hahn, Anti-Flt1 peptide—Hyaluronate conjugate for the treatment of retinal neovascularization and diabetic retinopathy, Biomaterials. 32 (2011) 3115-3123. doi:10.1016/j.biomaterials.2011.01.003.

[44] A. Bochot, E. Fattal, Liposomes for intravitreal drug delivery: a state of the art., J. Control. Release. 161 (2012) 628-34. doi:10.1016/j.jconrel.2012.01.019.

[45] T. Yasukawa, Y. Ogura, Y. Tabata, H. Kimura, P. Wiedemann, Y. Honda, Drug delivery systems for vitreoretinal diseases., Prog. Retin. Eye Res. 23 (2004) 253-81. doi: 10.1016/j.preteyeres.2004.02.003.

[46] F. M. Veronese, G. Pasut, PEGylation, successful approach to drug delivery, Drug Discov. Today. 10 (2005) 1451-1458.

[47] E. W. M. Ng, D. T. Shima, P. Calias, E. T. Cunningham, D. R. Guyer, A. P. Adamis, Pegaptanib, a targeted anti-VEGF aptamer for ocular vascular disease., Nat. Rev. Drug Discov. 5 (2006) 123-32. doi:10.1038/nrd1955.

[48] P. Bishop, The biochemical structure of mammalian vitreous, Eye. 10 (1996) 664-670. doi:10.1038/eye.1996.159.

[49] D. Park, Y. Kim, H Kim, K. Kim, Y.-S. Lee, J. Choe, et al., Hyaluronic acid promotes angiogenesis by inducing RHAMM-TGFβ receptor interaction via CD44-PKCδ, Mol. Cells. 33 (2012) 563-574. doi:10.1007/s10059-012-2294-1.

[50] U. Laurent, P. Tornquist, K. Granath, K. Lilja-Englind, D. Ytterberg, Molecular weight and concentration of hyaluronan in vitreous humour from diabetic patients, Acta Ophthalmol. 68 (1990) 109-112. doi:10.1111/j.1755-3768.1990.tb01972.x.

[51] G. A. Lutty, D. C. Thompson, J. Y. Gallup, R. J. Mello, A. Patz, A. Fenselau, Vitreous: An Inhibitor of Retinal Extract-Induced Neovascularization, Investig. Ophthalmol. Vis. Sci. 24 (1983) 52-56.

Example 3: Generation of Multivalent Conjugates with Anti-VEGF VHH or with Single-Chain Variable Fragment (scFv) Anti-VEGF (Anti-VEGF scFv)

Two multivalent conjugates made from two different anti-VEGF antibody formats were generated: a single-chain variable fragment (scFv) anti-VEGF antibody and a single-domain camelid (VHH) anti-VEGF antibody.

FIG. 20A-C:

The ability of each antibody conjugate to bind human 500 pg of VEGF-$A_{165}$ was compared to the corresponding unconjugated antibody using an ELISA assay. Both multivalent conjugates were made with 860 kDa hyaluronic acid (HyA). The valencies of scFv anti-VEGF antibody and VHH anti-VEGF antibody were 31 and 28, respectively. The data was fit using a four-parameter logistic curve and used to calculate the IC50 for each treatment. FIG. 20A shows percent unbound VEGF for unconjugated scFv anti-VEGF antibody and conjugated multivalent scFv anti-VEGF antibody. FIG. 20B shows percent unbound VEGF for unconjugated VHH anti-VEGF antibody and conjugated multivalent VHH anti-VEGF antibody. FIG. 20C shows the IC50 values for the conjugated antibodies of FIG. 20A-B compared to the unconjugated antibodies of FIG. 20A-B. Multivalent conjugation did not have a substantial effect on the IC50 values for the conjugates compared to the unconjugated antibody, as summarized in the FIG. 20C.

Example 4: Anti-VEGF VHH Multivalent (mvAnti-VEGF) Conjugates Made with HyA Show Increased Half-Life In Vitro and In Vivo The diffusion rates of unconjugated anti-VEGF antibody VHH and multivalent anti-VEGF antibody VHH (28 VHH per 860 kDa HyA) were compared by fluorescently tagging the proteins and entrapping them within a 1% HyA-PEG hydrogel made from commercially available components (BioTime). Swelling ratio and the mean molecular weight between crosslinks was estimated. The average mesh diameter of the hydrogel was estimated to be approximately 80 nm.

Figure 21:
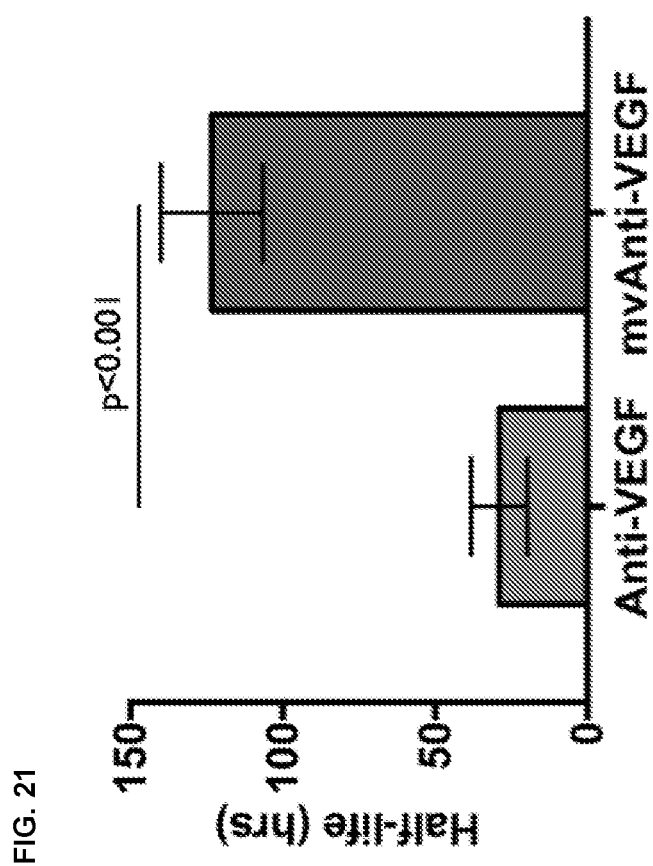
FIG. 21 depicts the half-life of the conjugated multivalent VHH anti-VEGF antibody compared to the unconjugated VHH anti-VEGF antibody.

FIG. 21:

The concentration of unconjugated protein and protein conjugate released from the hydrogels was measured every 2-3 days and the data were fit to an exponential decay curve to estimate their diffusion half-life. The half-life of the VHH anti-VEGF antibody conjugates was approximately 4-fold longer than that of the unconjugated VHH anti-VEGF antibody. The results shown in FIG. 21 are the mean of three independently repeated experiments.

The in vivo residence times of the unconjugated VHH anti-VEGF antibody and multivalent VHH anti-VEGF antibody conjugates were compared after injection into rat eyes. In this experiment, all of the VHH anti-VEGF antibody was fluorescently tagged as a reporter for concentration measurements, and 4 independent batches of mvAnti-VEGF were used (860 kDa MW HyA and with valencies in the range of 24 to 45). In each eye, 5 µL of a 275 µg/mL solution of either VHH anti-VEGF antibody or multivalent VHH anti-VEGF antibody conjugate was injected. Each eye received a total of 1.375 µg VHH anti-VEGF antibody either unconjugated or conjugated at any valency. At 0.5, 4, 22 and 45 hours after injection, rats were euthanized and enucleated their eyes as follows: n=8 eyes (0.5 hr), n=8 eyes (4 hr), n=4 eyes (22 hr), and n=2 eyes (45 hr).

Figures 22A, 22B:
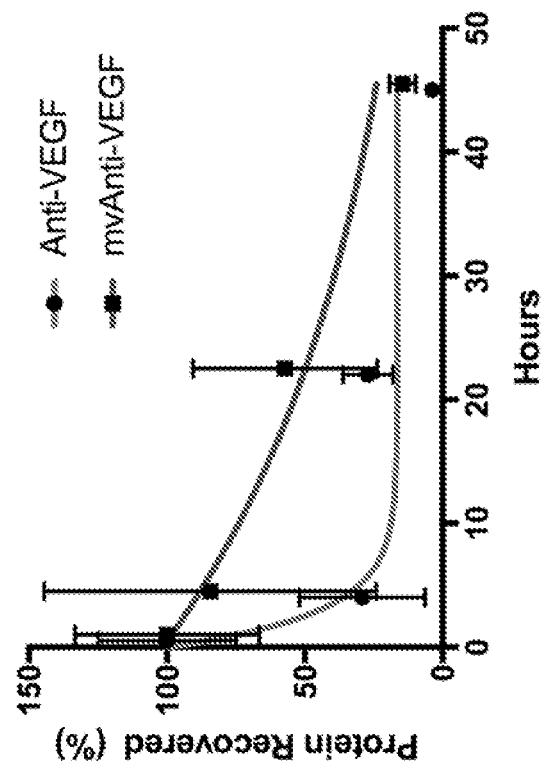
FIG. 22A-22B depicts the in vivo residence time and percent protein recovered of the conjugated multivalent VHH anti-VEGF antibody and the unconjugated VHH anti-VEGF antibody after injection into rat eyes.

FIG. 22A shows the percent protein recovered for unconjugated VHH and multivalent VHH anti-VEGF antibody conjugates. FIG. 22B shows the half-life of the unconjugated VHH anti-VEGF antibody and the conjugated multivalent VHH anti-VEGF antibody. Results show that conjugated multivalent VHH anti-VEGF antibody had an in vivo half-life of 21.9 hours compared to 1.9 hours for the unconjugated VHH anti-VEGF antibody.

Figures 23A, 23B:
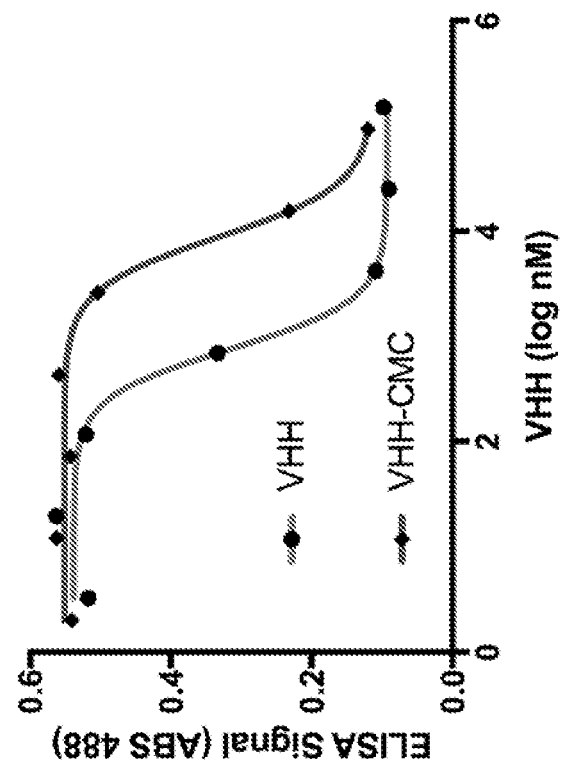
FIG. 23A-23B compare the ability of conjugated multivalent VHH anti-VEGF antibody and conjugated multivalent VHH anti-VEGF antibody with carboxymethylcellulose (CMC) to bind to VEGF-$A_{165}$ using an ELISA assay.

Example 5: Generation of VHH Anti-VEGF Antibody Multivalent Conjugates Made with Carboxymethylcellulose FIG. 23A-B show generation of a multivalent conjugate made from ~17 repeats of a single-domain camelid (VHH) antibody and carboxymethylcellulose (CMC, ~700 kDa). The ability of this anti-VEGF antibody (anti-VEGF VHH-CMC) conjugate to bind human 500 pg of VEGF-A165 was compared to the corresponding unconjugated VHH anti-VEGF antibody using an ELISA assay as shown in FIG. 23A. The data were fit using a four-parameter logistic curve and used to calculate the IC50 for each treatment, as shown in FIG. 23B.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating an ocular disease or disorder in an individual, the method comprising administering to the individual an effective amount of a conjugate comprising:
   a) a biologically active polypeptide having a molecular weight of from about 5 kDa to about 250 kDa, wherein the biologically active polypeptide is a single-chain Fv (scFv) anti-vascular endothelial growth factor (VEGF) antibody or a single-domain camelid (VHH) anti-VEGF antibody; and
   b) a biocompatible polymer comprising hyaluronic acid having a molecular weight of from about 500 kDa to about 1 MDa,
   wherein the polypeptide is covalently linked to the polymer directly or via a linker, and wherein the molar ratio of the biologically active polypeptide to the polymer is at least 25:1,
   wherein said administering is by intravitreal administration.

2. The method of claim 1, wherein the molar ratio of the biologically active polypeptide to the polymer is from 25:1 to 50:1.

3. The method of claim 1, wherein the vitreous half-life of the conjugate is at least 7 days.

4. The method of claim 1, wherein the individual is a human.

5. The method of claim 1, wherein the ocular disorder is macular degeneration, choroidal neovascularization, retinal neovascularization, proliferative vitreoretinopathy, glaucoma, or ocular inflammation.

6. The method of claim 1, wherein the conjugate is administered once every two months, once every three months, once every 6 months, or once a year.

7. The method of claim 1, wherein the vitreous half-life of the conjugate is at least 5-fold greater than the half-life of the biologically active polypeptide not conjugated to the biocompatible polymer.

8. The method of claim 1, wherein the vitreous half-life of the conjugate is from about one week to about 2 weeks.

9. The method of claim 1, wherein
   a) the biologically active polypeptide is a VHH anti-VEGF antibody; and
   b) the biocompatible polymer comprises hyaluronic acid having a molecular weight of from 750 kDa to 1 MDa,
   wherein the polypeptide is covalently linked to the polymer directly or via a linker, and
   wherein the molar ratio of the biologically active polypeptide to the polymer is at least 25:1.

10. The method of claim 1, wherein
    a) the biologically active polypeptide is a VHH anti-VEGF antibody; and
    b) the biocompatible polymer comprises hyaluronic acid having a molecular weight of from 750 kDa to 1 MDa,
    wherein the polypeptide is covalently linked to the polymer directly or via a linker, and
    wherein the molar ratio of the biologically active polypeptide to the polymer is at least 40:1.

11. The method of claim 1, wherein
    a) the biologically active polypeptide is a VHH anti-VEGF antibody; and
    b) the biocompatible polymer comprises hyaluronic acid having a molecular weight of from 750 kDa to 1 MDa,
    wherein the polypeptide is covalently linked to the polymer directly or via a linker, and
    wherein the molar ratio of the biologically active polypeptide to the polymer is from 40:1 to 60:1.

12. The method of claim 1, wherein the vitreous half-life of the conjugate is from about 2 weeks to about 4 weeks.

* * * * *

SEQUENCE LISTING

```
<160> NUMBER OF SEQ ID NOS: 8

<210> SEQ ID NO 1
<211> LENGTH: 755
<212> TYPE: PRT
<213> ORGANISM: Homo sapiens

<400> SEQUENCE: 1

Gly Ser Lys Leu Lys Asp Pro Glu Leu Ser Leu Lys Gly Thr Gln His
1               5                   10                  15

Ile Met Gln Ala Gly Gln Thr Leu His Leu Gln Cys Arg Gly Glu Ala
            20                  25                  30

Ala His Lys Trp Ser Leu Pro Glu Met Val Ser Lys Glu Ser Glu Arg
        35                  40                  45

Leu Ser Ile Thr Lys Ser Ala Cys Gly Arg Asn Gly Lys Gln Phe Cys
    50                  55                  60

Ser Thr Leu Thr Leu Asn Thr Ala Gln Ala Asn His Thr Gly Phe Tyr
65                  70                  75                  80

Ser Cys Lys Tyr Leu Ala Val Pro Thr Ser Lys Lys Lys Glu Thr Glu
                85                  90                  95

Ser Ala Ile Tyr Ile Phe Ile Ser Asp Thr Gly Arg Pro Phe Val Glu
            100                 105                 110

Met Tyr Ser Glu Ile Pro Glu Ile Ile His Met Thr Glu Gly Arg Glu
        115                 120                 125

Leu Val Ile Pro Cys Arg Val Thr Ser Pro Asn Ile Thr Val Thr Leu
    130                 135                 140

Lys Lys Phe Pro Leu Asp Thr Leu Ile Pro Asp Gly Lys Arg Ile Ile
145                 150                 155                 160

Trp Asp Ser Arg Lys Gly Phe Ile Ile Ser Asn Ala Thr Tyr Lys Glu
                165                 170                 175

Ile Gly Leu Leu Thr Cys Glu Ala Thr Val Asn Gly His Leu Tyr Lys
            180                 185                 190

Thr Asn Tyr Leu Thr His Arg Gln Thr Asn Thr Ile Ile Asp Val Gln
        195                 200                 205

Ile Ser Thr Pro Arg Pro Val Lys Leu Leu Arg Gly His Thr Leu Val
    210                 215                 220

Leu Asn Cys Thr Ala Thr Thr Pro Leu Asn Thr Arg Val Gln Met Thr
225                 230                 235                 240

Trp Ser Tyr Pro Asp Glu Lys Asn Lys Arg Ala Ser Val Arg Arg Arg
                245                 250                 255

Ile Asp Gln Ser Asn Ser His Ala Asn Ile Phe Tyr Ser Val Leu Thr
            260                 265                 270
```

```
Ile Asp Lys Met Gln Asn Lys Asp Lys Gly Leu Tyr Thr Cys Arg Val
            275                 280                 285

Arg Ser Gly Pro Ser Phe Lys Ser Val Asn Thr Ser Val His Ile Tyr
            290                 295                 300

Asp Lys Ala Phe Ile Thr Val Lys His Arg Lys Gln Gln Val Leu Glu
305                 310                 315                 320

Thr Val Ala Gly Lys Arg Ser Tyr Arg Leu Ser Met Lys Val Lys Ala
                325                 330                 335

Phe Pro Ser Pro Glu Val Val Trp Leu Lys Asp Gly Leu Pro Ala Thr
            340                 345                 350

Glu Lys Ser Ala Arg Tyr Leu Thr Arg Gly Tyr Ser Leu Ile Ile Lys
            355                 360                 365

Asp Val Thr Glu Glu Asp Ala Gly Asn Tyr Thr Ile Leu Leu Ser Ile
370                 375                 380

Lys Gln Ser Asn Val Phe Lys Asn Leu Thr Ala Thr Leu Ile Val Asn
385                 390                 395                 400

Val Lys Pro Gln Ile Tyr Glu Lys Ala Val Ser Ser Phe Pro Asp Pro
                405                 410                 415

Ala Leu Tyr Pro Leu Gly Ser Arg Gln Ile Leu Thr Cys Thr Ala Tyr
            420                 425                 430

Gly Ile Pro Gln Pro Thr Ile Lys Trp Phe Trp His Pro Cys Asn His
            435                 440                 445

Asn His Ser Glu Ala Arg Cys Asp Phe Cys Ser Asn Asn Glu Glu Ser
            450                 455                 460

Phe Ile Leu Asp Ala Asp Ser Asn Met Gly Asn Arg Ile Glu Ser Ile
465                 470                 475                 480

Thr Gln Arg Met Ala Ile Ile Glu Gly Lys Asn Lys Met Ala Ser Thr
                485                 490                 495

Leu Val Val Ala Asp Ser Arg Ile Ser Gly Ile Tyr Ile Cys Ile Ala
            500                 505                 510

Ser Asn Lys Val Gly Thr Val Gly Arg Asn Ile Ser Phe Tyr Ile Thr
            515                 520                 525

Asp Val Pro Asn Gly Phe His Val Asn Leu Glu Lys Met Pro Thr Glu
            530                 535                 540

Gly Glu Asp Leu Lys Leu Ser Cys Thr Val Asn Lys Phe Leu Tyr Arg
545                 550                 555                 560

Asp Val Thr Trp Ile Leu Leu Arg Thr Val Asn Asn Arg Thr Met His
                565                 570                 575

Tyr Ser Ile Ser Lys Gln Lys Met Ala Ile Thr Lys Glu His Ser Ile
            580                 585                 590

Thr Leu Asn Leu Thr Ile Met Asn Val Ser Leu Gln Asp Ser Gly Thr
            595                 600                 605

Tyr Ala Cys Arg Ala Arg Asn Val Tyr Thr Gly Glu Glu Ile Leu Gln
            610                 615                 620

Lys Lys Glu Ile Thr Ile Arg Asp Gln Glu Ala Pro Tyr Leu Leu Arg
625                 630                 635                 640

Asn Leu Ser Asp His Thr Val Ala Ile Ser Ser Ser Thr Thr Leu Asp
                645                 650                 655

Cys His Ala Asn Gly Val Pro Glu Pro Gln Ile Thr Trp Phe Lys Asn
            660                 665                 670

Asn His Lys Ile Gln Gln Glu Pro Gly Ile Ile Leu Gly Pro Gly Ser
            675                 680                 685

Ser Thr Leu Phe Ile Glu Arg Val Thr Glu Glu Asp Glu Gly Val Tyr
```

```
                690              695              700
His Cys Lys Ala Thr Asn Gln Lys Gly Ser Val Glu Ser Ser Ala Tyr
705              710              715              720

Leu Thr Val Gln Gly Thr Ser Asp Lys Ser Asn Leu Glu Leu Ile Thr
                725              730              735

Leu Thr Cys Thr Cys Val Ala Ala Thr Leu Phe Trp Leu Leu Leu Thr
                740              745              750

Leu Phe Ile
        755

<210> SEQ ID NO 2
<211> LENGTH: 303
<212> TYPE: PRT
<213> ORGANISM: Homo sapiens

<400> SEQUENCE: 2

Gly Ser Lys Leu Lys Asp Pro Glu Leu Ser Leu Lys Gly Thr Gln His
1               5                   10                  15

Ile Met Gln Ala Gly Gln Thr Leu His Leu Gln Cys Arg Gly Glu Ala
            20                  25                  30

Ala His Lys Trp Ser Leu Pro Glu Met Val Ser Lys Glu Ser Glu Arg
        35                  40                  45

Leu Ser Ile Thr Lys Ser Ala Cys Gly Arg Asn Gly Lys Gln Phe Cys
    50                  55                  60

Ser Thr Leu Thr Leu Asn Thr Ala Gln Ala Asn His Thr Gly Phe Tyr
65                  70                  75                  80

Ser Cys Lys Tyr Leu Ala Val Pro Thr Ser Lys Lys Lys Glu Thr Glu
                85                  90                  95

Ser Ala Ile Tyr Ile Phe Ile Ser Asp Thr Gly Arg Pro Phe Val Glu
            100                 105                 110

Met Tyr Ser Glu Ile Pro Glu Ile Ile His Met Thr Glu Gly Arg Glu
        115                 120                 125

Leu Val Ile Pro Cys Arg Val Thr Ser Pro Asn Ile Thr Val Thr Leu
    130                 135                 140

Lys Lys Phe Pro Leu Asp Thr Leu Ile Pro Asp Gly Lys Arg Ile Ile
145                 150                 155                 160

Trp Asp Ser Arg Lys Gly Phe Ile Ile Ser Asn Ala Thr Tyr Lys Glu
                165                 170                 175

Ile Gly Leu Leu Thr Cys Glu Ala Thr Val Asn Gly His Leu Tyr Lys
            180                 185                 190

Thr Asn Tyr Leu Thr His Arg Gln Thr Asn Thr Ile Ile Asp Val Gln
        195                 200                 205

Ile Ser Thr Pro Arg Pro Val Lys Leu Leu Arg Gly His Thr Leu Val
    210                 215                 220

Leu Asn Cys Thr Ala Thr Thr Pro Leu Asn Thr Arg Val Gln Met Thr
225                 230                 235                 240

Trp Ser Tyr Pro Asp Glu Lys Asn Lys Arg Ala Ser Val Arg Arg Arg
                245                 250                 255

Ile Asp Gln Ser Asn Ser His Ala Asn Ile Phe Tyr Ser Val Leu Thr
            260                 265                 270

Ile Asp Lys Met Gln Asn Lys Asp Lys Gly Leu Tyr Thr Cys Arg Val
        275                 280                 285

Arg Ser Gly Pro Ser Phe Lys Ser Val Asn Thr Ser Val His Ile
    290                 295                 300
```

<210> SEQ ID NO 3
<211> LENGTH: 187
<212> TYPE: PRT
<213> ORGANISM: Homo sapiens

<400> SEQUENCE: 3

Ile Pro Glu Ile Ile His Met Thr Glu Gly Arg Glu Leu Val Ile Pro
1               5                   10                  15

Cys Arg Val Thr Ser Pro Asn Ile Thr Val Thr Leu Lys Lys Phe Pro
                20                  25                  30

Leu Asp Thr Leu Ile Pro Asp Gly Lys Arg Ile Ile Trp Asp Ser Arg
            35                  40                  45

Lys Gly Phe Ile Ile Ser Asn Ala Thr Tyr Lys Glu Ile Gly Leu Leu
    50                  55                  60

Thr Cys Glu Ala Thr Val Asn Gly His Leu Tyr Lys Thr Asn Tyr Leu
65                  70                  75                  80

Thr His Arg Gln Thr Asn Thr Ile Ile Asp Val Gln Ile Ser Thr Pro
                85                  90                  95

Arg Pro Val Lys Leu Leu Arg Gly His Thr Leu Val Leu Asn Cys Thr
                100                 105                 110

Ala Thr Thr Pro Leu Asn Thr Arg Val Gln Met Thr Trp Ser Tyr Pro
            115                 120                 125

Asp Glu Lys Asn Lys Arg Ala Ser Val Arg Arg Ile Asp Gln Ser
130                 135                 140

Asn Ser His Ala Asn Ile Phe Tyr Ser Val Leu Thr Ile Asp Lys Met
145                 150                 155                 160

Gln Asn Lys Asp Lys Gly Leu Tyr Thr Cys Arg Val Arg Ser Gly Pro
                165                 170                 175

Ser Phe Lys Ser Val Asn Thr Ser Val His Ile
            180                 185

<210> SEQ ID NO 4
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 4

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu

```
            130                 135                 140
Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
                195                 200                 205

Ala Thr Val Asn Gly His Leu Tyr Lys Thr Asn Tyr Leu Thr His Arg
            210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
            290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Cys Asp Asp Asp Lys His His His His His
                340                 345                 350

<210> SEQ ID NO 5
<211> LENGTH: 280
<212> TYPE: PRT
<213> ORGANISM: Artificial sequence
<220> FEATURE:
<223> OTHER INFORMATION: Synthetic polypeptide

<400> SEQUENCE: 5

Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Ile Ile His Ser
            20                  25                  30

Trp Leu Ala Trp Tyr Gln Gln Lys Pro Gly Lys Ala Pro Lys Leu Leu
        35                  40                  45

Ile Tyr Leu Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Val Tyr Leu Ala Ser
                85                  90                  95

Thr Asn Gly Ala Asn Phe Gly Gln Gly Thr Lys Leu Thr Val Leu Gly
            100                 105                 110

Gly Gly Gly Gly Ser Gly Gly Gly Ser Gly Gly Gly Gly Ser Gly
        115                 120                 125

Gly Gly Gly Ser Glu Val Gln Leu Val Glu Ser Gly Gly Gly Leu Val
        130                 135                 140

Gln Pro Gly Gly Ser Leu Arg Leu Ser Cys Thr Ala Ser Gly Phe Ser
```

```
                145                 150                 155                 160
Leu Thr Asp Tyr Tyr Tyr Met Thr Trp Val Arg Gln Ala Pro Gly Lys
                165                 170                 175

Gly Leu Glu Trp Val Gly Phe Ile Asp Pro Asp Asp Pro Tyr Tyr
            180                 185                 190

Ala Thr Trp Ala Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
            210                 215                 220

Val Tyr Tyr Cys Ala Gly Gly Asp His Asn Ser Gly Trp Gly Leu Asp
225                 230                 235                 240

Ile Trp Gly Gln Gly Thr Leu Val Thr Val Ser Ser Pro Ser Thr
                245                 250                 255

Pro Pro Thr Pro Ser Pro Ser Thr Pro Pro Gly Gly Cys Asp Asp Asp
            260                 265                 270

Asp Lys His His His His His His
            275                 280

<210> SEQ ID NO 6
<211> LENGTH: 156
<212> TYPE: PRT
<213> ORGANISM: Artificial sequence
<220> FEATURE:
<223> OTHER INFORMATION: Synthetic polypeptide

<400> SEQUENCE: 6

Ser Asn Ala Asp Val Gln Leu Val Glu Ser Gly Gly Gly Leu Val Gln
1               5                   10                  15

Pro Gly Gly Ser Leu Arg Leu Ser Cys Ala Ala Ser Gly Arg Thr Phe
            20                  25                  30

Ser Ser Tyr Ser Met Gly Trp Phe Arg Gln Ala Pro Gly Lys Glu Arg
        35                  40                  45

Glu Phe Val Val Ala Ile Ser Lys Gly Gly Tyr Lys Tyr Asp Ala Val
    50                  55                  60

Ser Leu Glu Gly Arg Phe Thr Ile Ser Arg Asp Asn Ala Lys Asn Thr
65                  70                  75                  80

Val Tyr Leu Gln Ile Asn Ser Leu Arg Pro Glu Asp Thr Ala Val Tyr
                85                  90                  95

Tyr Cys Ala Ser Ser Arg Ala Tyr Gly Ser Ser Arg Leu Arg Leu Ala
            100                 105                 110

Asp Thr Tyr Glu Tyr Trp Gly Gln Gly Thr Leu Val Thr Val Ser Ser
        115                 120                 125

Ser Pro Ser Thr Pro Pro Thr Pro Ser Pro Ser Thr Pro Pro Gly Gly
    130                 135                 140

Cys Asp Asp Asp Asp Lys His His His His His His
145                 150                 155

<210> SEQ ID NO 7
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 7

Asp Asp Asp Asp Lys
1               5
```

```
<210> SEQ ID NO 8
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 8

His His His His His His
1               5
```